US011849964B2

(12) United States Patent
Davis et al.

(10) Patent No.: US 11,849,964 B2
(45) Date of Patent: Dec. 26, 2023

(54) ANATOMICAL EXTRACTION DEVICE

(71) Applicant: C.R. Bard, Inc., Murray Hill, NJ (US)

(72) Inventors: Brandt Michael Davis, Milford, OH (US); Jeffrey Edward Franklin, Liberty Township, OH (US)

(73) Assignee: C. R. Bard, Inc., Murray Hill, NJ (US)

( * ) Notice: Subject to any disclaimer, the term of this patent is extended or adjusted under 35 U.S.C. 154(b) by 408 days.

(21) Appl. No.: 16/978,013

(22) PCT Filed: Mar. 15, 2019

(86) PCT No.: PCT/US2019/022585
§ 371 (c)(1),
(2) Date: Sep. 3, 2020

(87) PCT Pub. No.: WO2019/178543
PCT Pub. Date: Sep. 19, 2019

(65) Prior Publication Data
US 2020/0405335 A1 Dec. 31, 2020

Related U.S. Application Data

(60) Provisional application No. 62/643,644, filed on Mar. 15, 2018.

(51) Int. Cl.
A61B 17/221 (2006.01)
(52) U.S. Cl.
CPC .... A61B 17/221 (2013.01); A61B 2017/2212 (2013.01)
(58) Field of Classification Search
CPC ............ A61B 17/221; A61B 17/22031; A61B 17/32056; A61B 17/50; A61B 2017/2212; A61B 2017/2215; A61B 2017/00867
(Continued)

(56) References Cited

U.S. PATENT DOCUMENTS 5,906,622 A    5/1999 Lippitt et al.
5,924,175 A *  7/1999 Lippitt ................. A61B 17/221
                                                    24/537
(Continued)

FOREIGN PATENT DOCUMENTS

WO    2019178543 A1    9/2019

OTHER PUBLICATIONS

European Patent Office, extended European search report in EP19767591.1, dated Oct. 15, 2021.
(Continued)

Primary Examiner — Kankindi Rwego
(74) Attorney, Agent, or Firm — Dorton & Willis LLP; Ryan Willis

(57) ABSTRACT

A medical extraction device comprising: (a) a sheath including a distal end configured to be inserted into a patient and a proximal end configured to be retained exteriorly of the patient; (b) a basket configured to extend from a distal end of the sheath and be repositionable between an expanded position and a retracted position, the basket including at least three loops, the basket also including a first guide and a second guide, where the first guide receives portions of the first loop and the third loop, where the second guide receives portions of the first loop and the second loop, where the second loop and the third loop are fixedly mounted to one another at a location interposing the first guide and the second guide; and, (c) a handle control operatively coupled to a proximal end of the sheath and being operatively coupled to the basket, the handle control configured facilitate repositioning of the basket with respect to the sheath between the retracted position and the expanded position.

30 Claims, 30 Drawing Sheets

(58) Field of Classification Search
USPC .................. 606/106, 113, 114, 127, 128
See application file for complete search history.

(56) References Cited

U.S. PATENT DOCUMENTS

| | | |
|---|---|---|
| 2003/0109889 A1 | 6/2003 | Mercereau et al. |
| 2007/0106304 A1 | 5/2007 | Hammack et al. |
| 2007/0135820 A1 | 6/2007 | Que et al. |
| 2014/0172008 A1 | 6/2014 | McKinnis et al. |
| 2015/0148814 A1 | 5/2015 | Chu |
| 2015/0164522 A1 | 6/2015 | Budiman et al. |
| 2016/0022290 A1 | 1/2016 | Johnson et al. |
| 2016/0278797 A1 | 9/2016 | Boston |

OTHER PUBLICATIONS

Saudi Authority for Intellectual Property, examination report in SA 520420149, notification dated Nov. 6, 2022.

* cited by examiner

ANATOMICAL EXTRACTION DEVICE

CROSS REFERENCE TO RELATED APPLICATIONS

The present application claims the benefit of U.S. Provisional Patent Application Ser. No. 62/643,644, titled, "ANATOMICAL EXTRACTION DEVICE," filed Mar. 15, 2018, the disclosure of which is incorporated herein by reference.

INTRODUCTION TO THE INVENTION

The present disclosure is directed to anatomical extraction devices and, more specifically, to anatomical extraction devices that may be used to extract objects within bodily canals and bodily reservoirs.

Small stones in the distal ureter may be reliably and definitively extracted with ureteroscopic stone basketing. Presently, a wide range of ureteroscopic baskets are commercially available. Many of these ureteroscopic baskets consist of wires slidably mounted in a tubular sleeve forming a canula. The distal ends of the wires may have free ends or be secured to one another and are capable of expanding when extended outwardly by virtue of the resiliency of the material comprising the wires. For those wires that are connected to one another, a distal plug may be present at the far distal tip of the basket. Those skilled in the art have theorized that the presence of a distal tip of a basket is disadvantageous because the tip creates distance from the end to the functional engaging portion of the basket, thus making stone entrapment more difficult. Also, those skilled in the art have lamented that certain baskets having distal tips can pierce the renal calyceal urothelial lining, thereby causing bleeding that obscures visualization and can lead to premature termination of stone extraction. Similar drawbacks have been noted in the art with respect to baskets with ends that are free, an example of which is disclosed in U.S. Pat. No. 6,416,519.

As a means to address the perceived drawbacks of a basket having a distal tip or with free distal ends, certain "open ended" baskets have been developed. Among these "open ended" baskets are the embodiments disclosed in U.S. Pat. No. 5,906,622. But the embodiments of U.S. Pat. No. 5,906,622 have one very pronounced disadvantage—the inability to affirmatively grab the intended object to be removed. Rather than grabbing the intended object by extending beyond and synching around the object, all of the embodiments of this '622 patent operate to pinch the object from the object's sides. Not surprisingly, this pinching operation is not depicted in the '622 patent. And this pinching operation is quite unsatisfactory because circumferential pressure on the baskets (which can be the result of drawing the baskets through a relative small diameter renal conduit) of the '622 patent causes the object to spurt out of the distal end of the basket. In other words, because the baskets of the '622 patent do not extend distally beyond the distal end of the object to be captured, such as a kidney stone, for example, there is no real ability to retard distal motion of the object with respect to the baskets when circumferential or proximal pressure is applied thereto.

Thus, there exists a need to provide an anatomical extraction device that is open-ended, but at the same time overcomes the problems noted above, that provides for a basket extending beyond and affirmatively grabbing an intended object.

It is a first aspect of the present invention to provide a medical extraction device comprising a hollow sheath including a distal end from which a basket may extend in an expanded position, the basket repositionable between a retracted position and the expanded position, the basket comprising: (i) a first guide and a second guide circumscribed by the hollow sheath; (ii) a first loop, a second loop, and a third loop, where the first loop extends between the first and second guides; (iii) a first anchor fixing a relative position of a distal portion of the second loop with respect to a distal portion of the third loop; (iv) a first joint coupling the second loop and the third loop proximal to the first anchor; (v) a second anchor fixing a relative position of a distal portion of the first loop with respect to a portion of the first guide; (vi) a line operatively coupled to proximal portions of at least two of the first, second, and third loops so that repositioning of the line is operative to at least one of increase and decrease the length of at least two of the first, second, and third loops extending from the distal end.

In a more detailed embodiment of the first aspect, the extraction device further includes a fourth loop and a third guide, where the fourth loop extends between the fourth and first guides, and the second loop extends between the second and third guide. In yet another more detailed embodiment, the extraction device further includes a handle control mounted to a proximal portion of the hollow sheath and configured to be handheld, the handle control including an actuator operatively coupled to the line so that repositioning of the actuator is operative to direct repositioning of the line. In a further detailed embodiment, the extraction device further includes a handle control repositionably mounted to a proximal portion of the hollow sheath, the handle control operatively coupled to the line so that repositioning of the handle control with respect to the hollow sheath is operative to direct repositioning of the line. In still a further detailed embodiment, the line comprises a plurality of lines, each of the plurality of lines being operatively coupled to at least one of the first, second, and third loops. In a more detailed embodiment, at least one of the first and second guides comprises a duct through which extends portions of at least two of the first, second, and third loops. In a more detailed embodiment, the first guide comprises a first duct through which portions of the first loop and the second loop extend, and the second guide comprises a second duct through which portions of the first loop and the second loop extend. In another more detailed embodiment, at least one of the first and second guides delineates a channel along which extends portions of at least two of the first, second, and third loops. In yet another more detailed embodiment, the first guide comprises a first channel along which portions of the first loop and the second loop extend, and the second guide comprises a second channel along which portions of the first loop and the second loop extend. In still another more detailed embodiment, at least one of the first, second, and third loops is discontinuous.

In yet another more detailed embodiment of the first aspect, the first guide and the second guide are at least one of repositionable and fixedly positioned with respect to the hollow sheath. In yet another more detailed embodiment, the first joint includes at least one of a weld, glue, solder, a wire twist, and a wire weave. In a further detailed embodiment, the first anchor comprises at least one of a weld, glue, solder, a wire twist, and a wire weave secured to at least one of the first guide, the second guide, and the hollow sheath. In still a further detailed embodiment, the first anchor and the second anchor comprise a common anchor. In a more detailed embodiment, a proximal portion of the first loop and a proximal portion of the third loop are freely repositionable with respect to the second guide. In a more detailed embodiment, the first loop is independently repositionable with respect to the second and third loops. In another more detailed embodiment, the first loop is dependently repositionable with respect to the second and third loops by way of the line.

It is a second aspect of the present invention to provide a method of operating a medical extraction device comprising: (a) increasing an exposed length of a first loop, a second loop, and a third loop extending from a hollow sheath, where the first loop, a second loop, and a third loop are operatively coupled to form a basket in an open position that includes an interior cavity predominantly delineated by a first plane spanning an arcuate portion of the first loop, a second plane spanning an arcuate portion of the second loop, a third plane spanning an arcuate portion of the third loop and a fourth plane spanning a distal most point of the first loop, a distal most point of the second loop, and a distal most point of the third loop, where a middle longitudinal cross-section of the cavity is taken at a midpoint of a longitudinal axis perpendicular to the fourth plane; and, (b) changing an exposed length of the second loop and the third loop so as to reposition a joint, where the second loop and the third loop are joined, in an arcuate path to decrease a cross-sectional area of the fourth plane at a rate greater than that of a cross-sectional area of the middle longitudinal cross-section In a more detailed embodiment of the second aspect, increasing the exposed length of the first loop, the second loop, and the third loop includes maintaining a relative position of a first guide and a second guide with respect to the hollow sheath, where the first loop extends between the first guide and the second guide. In yet another more detailed embodiment, increasing the exposed length of the first loop, the second loop, and the third loop includes repositioning a first guide and a second guide with respect to the hollow sheath, where the exposed length comprises a length of each loop extending from a respective guide beyond the hollow sheath.

It is a third aspect of the present invention to provide a method of operating a medical extraction device comprising: (a) repositioning a first loop, a second loop, and a third loop to delineate a receiving area extending beyond a distal end of a hollow sheath, the receiving area at a static state being tapered and having a cross-sectional area that decreases in a direction toward the hollow sheath, where the first loop, the second loop, and the third loop cooperate to delineate an opening at a distal end, where the opening allows passage of an object into the receiving area through the opening; and, (b) repositioning a joint, where at least two of the first loop, the second loop, and the third loop are joined, in an arcuate path to decrease a size of the opening and preclude an object within the receiving area from passing through the decreased size opening.

It is a fourth aspect of the present invention to provide a method of fabricating a medical extraction device comprising: (a) arranging at least one of a first loop, a second loop, and a third loop in a geometric configuration, where at least two of the loops are angled with respect to one another using the following equation A=360/N, where A refers to the angle between the at least two loops and N refers to the total number of loops; (b) positioning at least a first portion of the first loop and a first portion of the third loop at least one of along and within a first guide so that the first portions of the first and third loops are repositionable with respect to the first guide and with respect to each other; (c) positioning at least a first portion of the second loop and a second portion of the first loop at least one of along and within a second guide so that the second portion of the first loop is fixed with respect to the second guide, and the first portion of the second loop is repositionable with respect to the second guide and with respect to the first loop; (d) directly coupling at least a second portion of the third loop and a second portion of the second loop at a joint; (e) positioning the first loop, the second loop, and the third loop at least partially inside a hollow sheath so the hollow sheath at least partially circumscribes the first loop, the second loop, and the third loop; (f) operatively coupling a drive line to the first portions of the first, second, and third loops so that repositioning the drive line is operative to concurrently increase or decrease an exposed length of the first, second, and third loops extending beyond the hollow sheath.

It is a fifth aspect of the present invention to provide a medical extraction device comprising: (a) a sheath including a distal end configured to be inserted into a patient and a proximal end configured to be retained exteriorly of the patient; (b) a basket configured to extend from a distal end of the sheath and be repositionable between an expanded position and a retracted position, the basket including at least three loops, the basket also including a first guide and a second guide, where the first guide receives portions of the first loop and the third loop, where the second guide receives portions of the first loop and the second loop, where the second loop and the third loop are fixedly mounted to one another at a location interposing the first guide and the second guide; and, (c) a handle control operatively coupled to a proximal end of the sheath and being operatively coupled to the basket, the handle control configured facilitate repositioning of the basket with respect to the sheath between the retracted position and the expanded position.

DETAILED DESCRIPTION

It should be understood that the following detailed description of embodiments of the present invention are exemplary in nature and are not intended to constitute limitations upon the present invention. It is also to be understood that variations of the exemplary embodiments contemplated by one of ordinary skill in the art shall concurrently fall within the scope and spirit of the invention. It should also be understood that features across multiple embodiments may be combined, rearranged, and/or interchanged without departing from the scope of the instant disclosure.

Referencing FIGS. 1-10 and 22-24, a first exemplary embodiment of a medical extraction device 100 includes an elongated hollow sheath 102 from which extends at a distal end of thereof a repositionable basket 104. The basket 104 is operatively connected to a handle control 106 via a line 108 (that may comprise one or multiple lines), which extends through the hollow portion of the sheath and is longitudinally repositionable with respect to the sheath, to facilitate opening (i.e., an expanded position) and closing (i.e., a retracted position) of the basket. A proximal aspect of the sheath 102 may be fixed or repositionably mounted to the handle control 106.

Figure 1:
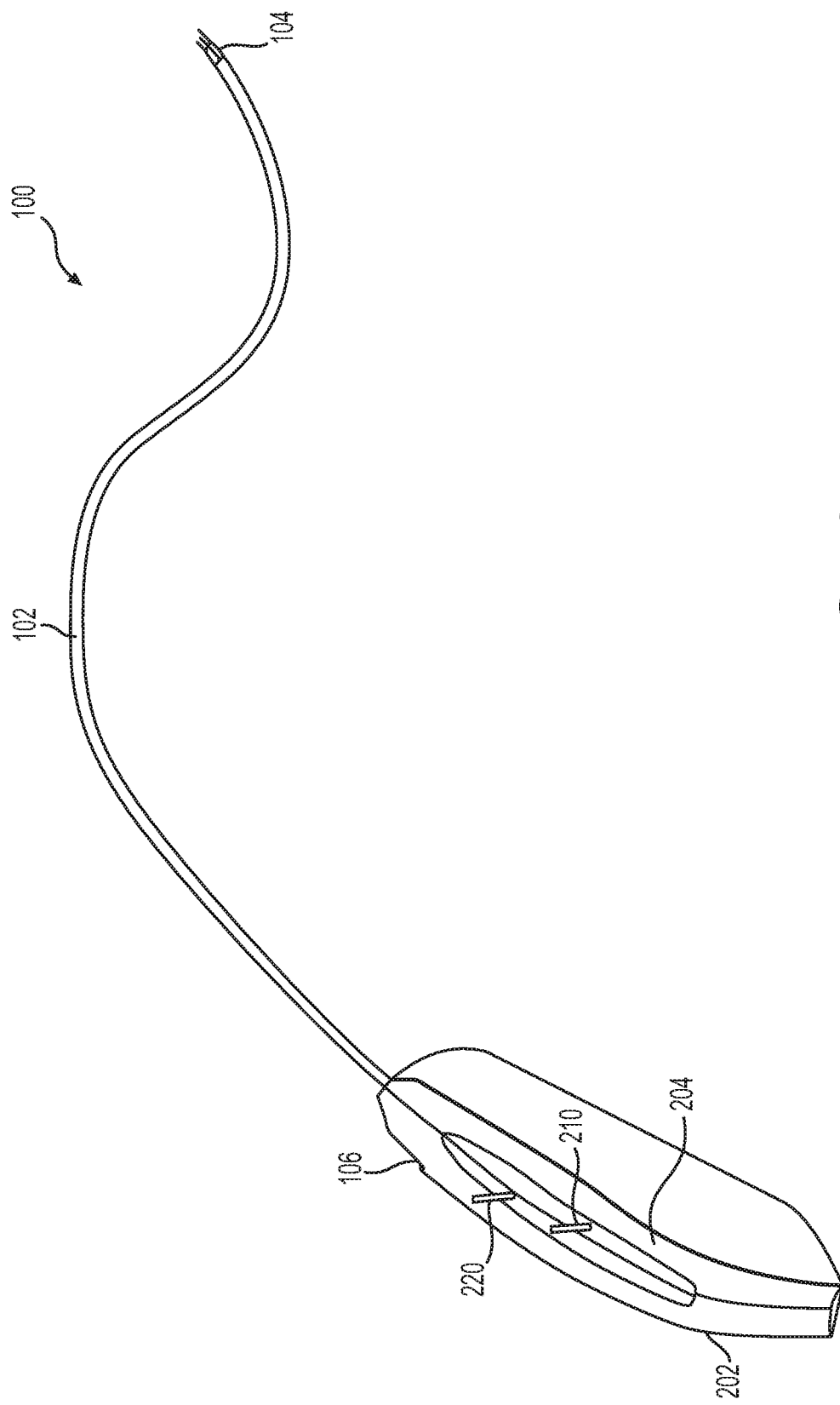
FIG. 1 is an elevated perspective view of a first exemplary medical extraction device in accordance with the instant disclosure.
Figure 2:
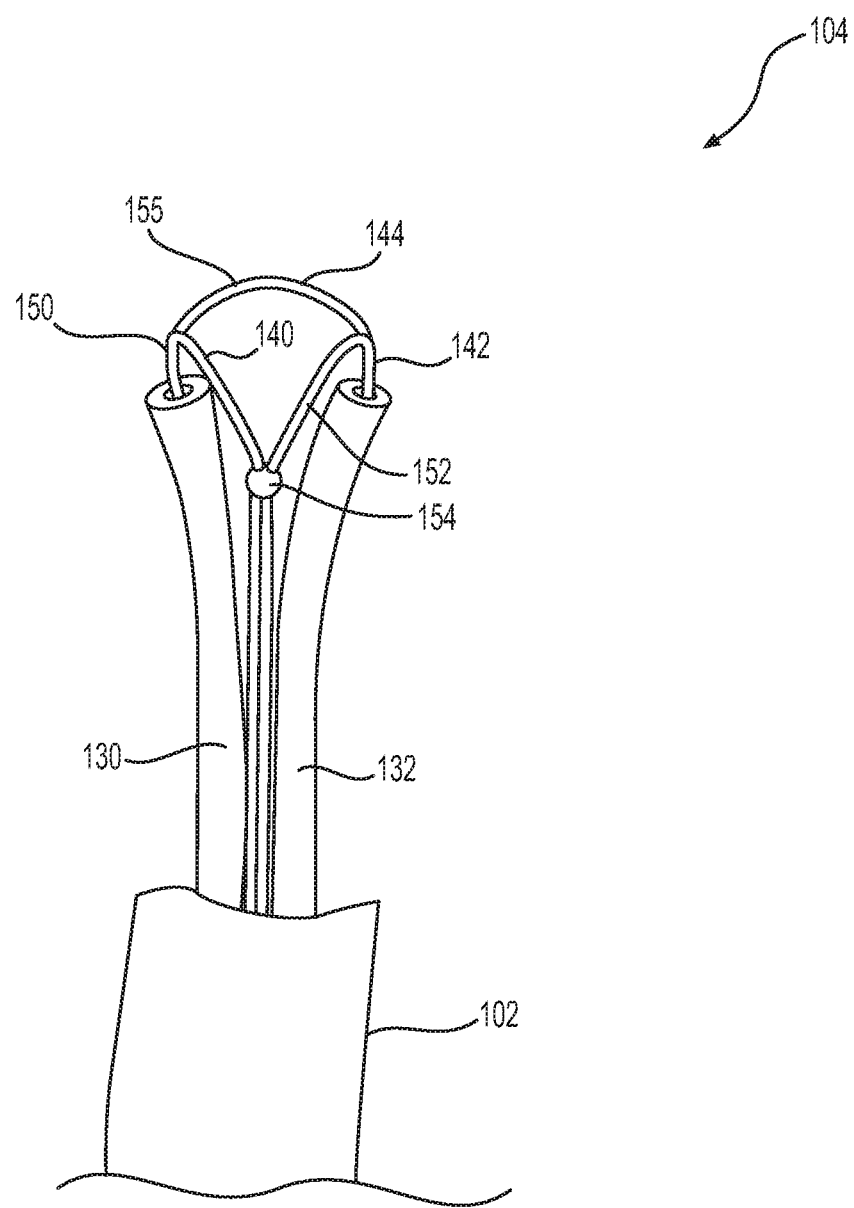
FIG. 2 is an isolated perspective view of a distal end of the first exemplary medical extraction device of FIG. 1 showing a basket extending beyond a sheath.
Figure 3:
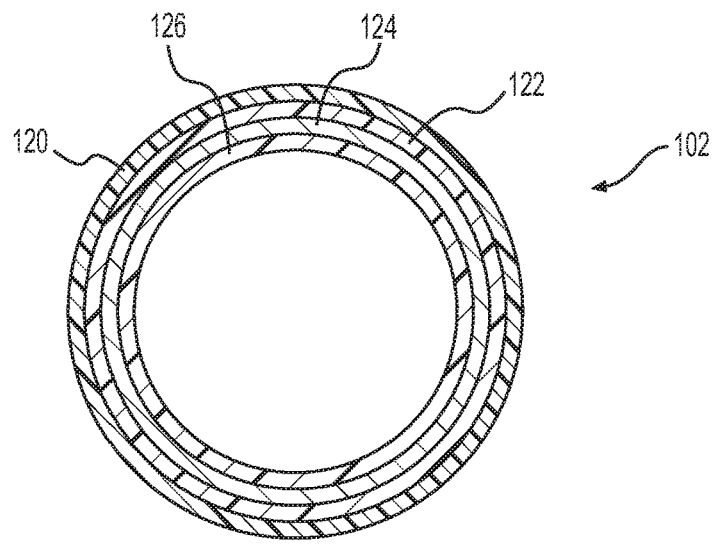
FIG. 3 is a cross-sectional view of the sheath of the first exemplary medical extraction device.

By way of example, turning to FIG. 3, the sheath 102 may be fabricated to provide a generally smooth, arcuate exterior periphery and a hollow interior channel. By way of example, the sheath 102 may comprise a multilayer construction that includes, from outermost to innermost, a layer of Teflon 120, a first polyimide layer 122, a stainless steel braid layer 124, and a second polyimide layer 126 demarcating the hollow interior channel. In exemplary form, the sheath 102 may have a substantially constant cross-section or a cross-section that changes along its longitudinal length. Moreover, the sheath 102 may have a circular cross-section, an oblong cross-section, or any other shaped cross-section that provides a longitudinal channel within which the line(s) 108 may be repositioned. By way of further example, the sheath 102 may have a maximum outside dimension ranging between 1.0 to 12.0 Fr. to, optionally, accommodate all or a portion of the basket 104 when in a retracted position.

Figure 4:
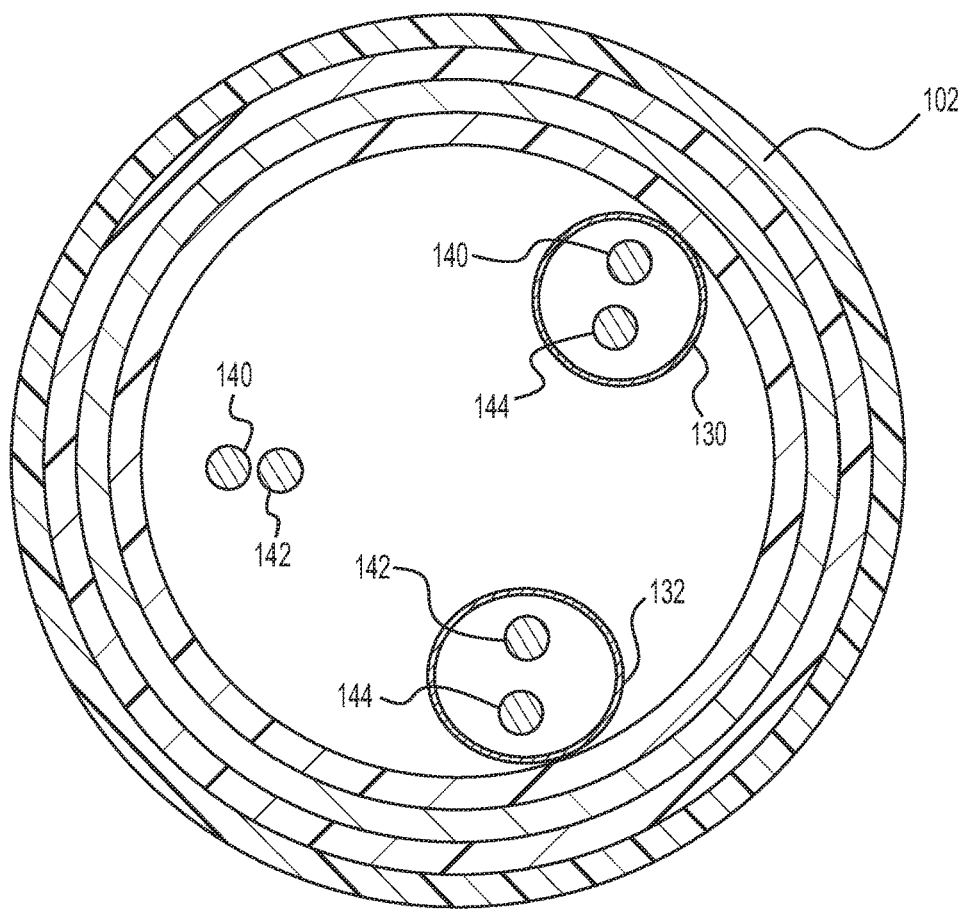
FIG. 4 is a cross-sectional view of exemplary components extending through a sheath taken just prior to a distal end of the sheath that shows the respective wires and guides where the guides are fixed relative to the sheath of the first exemplary medical extraction device.
Figure 5:
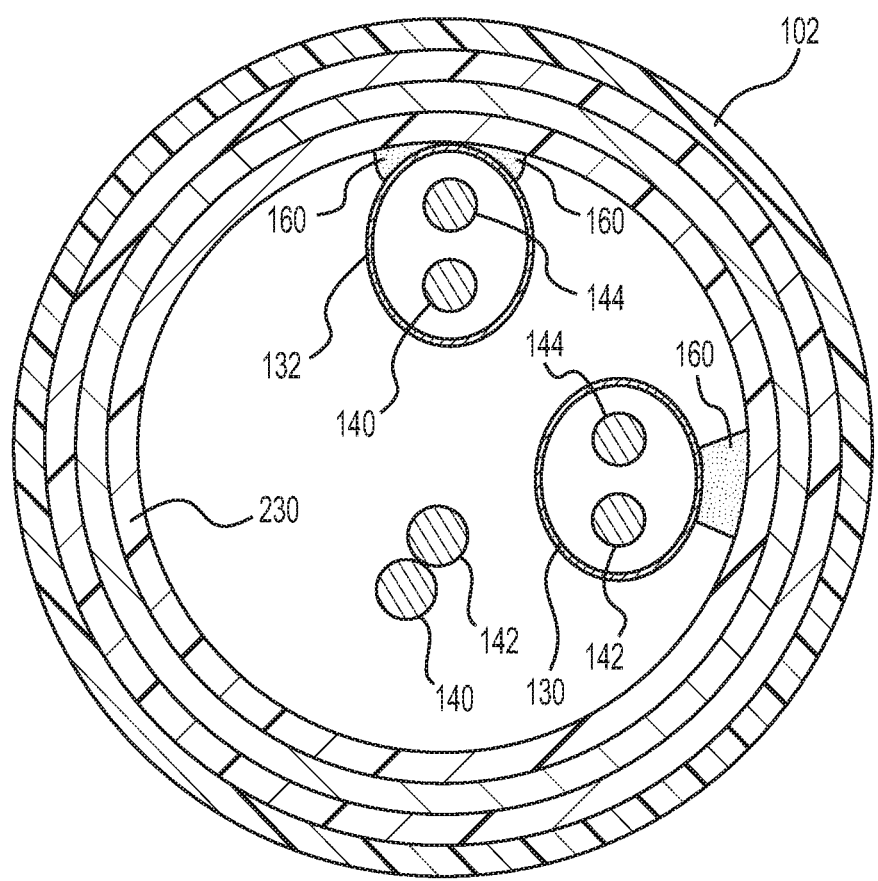
FIG. 5 is a cross-sectional view of exemplary components extending through a sheath taken just prior to a distal end of the sheath that shows the respective wires and guides where the guides are repositionable relative to the sheath of the first alternate exemplary medical extraction device.
Figure 6:
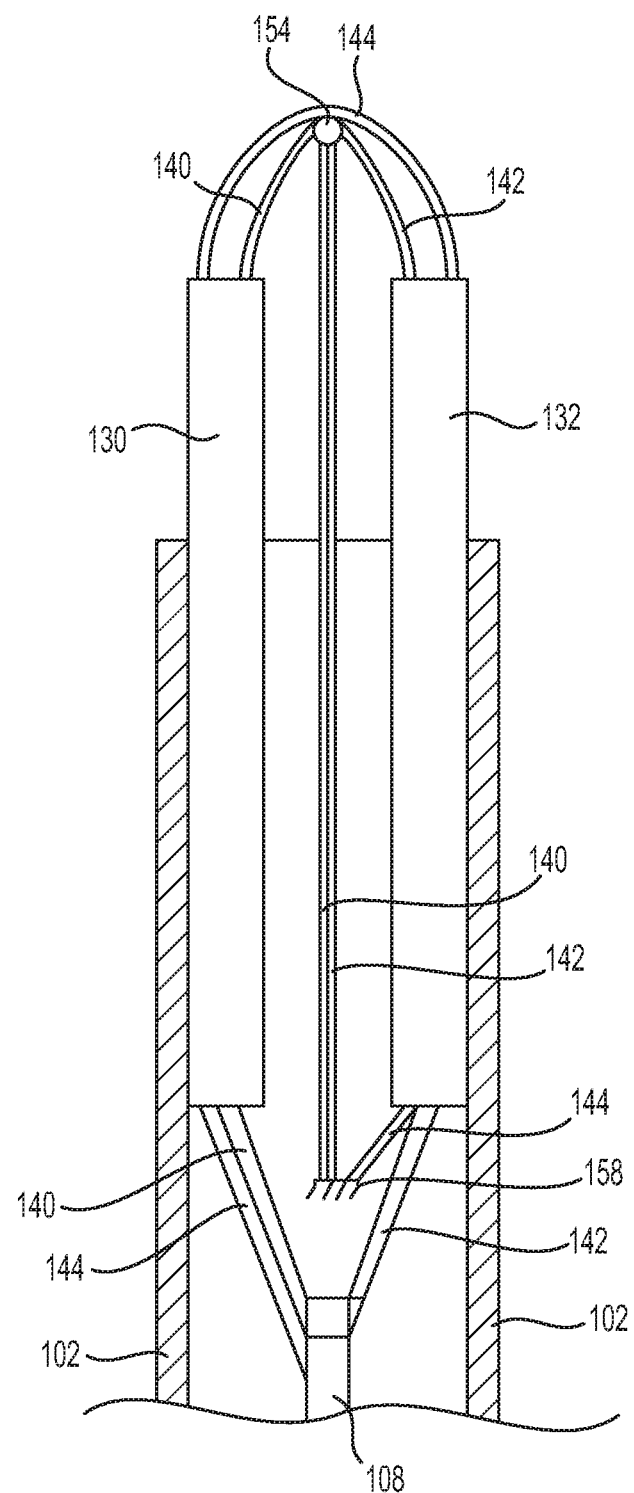
FIG. 6 is a cross-sectional view of an exemplary sheath and a perspective view of exemplary components extending through the sheath taken just prior to a distal end of the sheath that shows the respective wires and guides where the guides are fixed relative to the sheath of the first exemplary medical extraction device.

In exemplary form, with reference to FIG. 4, the basket 104 may comprise two or more guides 130, 132 through which extend two or more flexible wires 140, 142, 144. By way of example, the guides 130, 132 may each be fabricated from a suitable plastic material such as, without limitation, polyethylene, polypropylene, polyester, polyvinyl chloride, polyimide or the like. But it should also be noted that the guides 130, 132 may be fabricated from materials other than plastics such as, without limitation, metals and metal alloys. The guides 130, 132 may be deformable and, alternatively, elastically deformable. Each of the guides 130, 132 may be fixedly secured to the sheath 102 (such as by way of adhesive 160 or other bonding means) or may be repositionable with respect to the sheath. By way of further example, at least a portion of guides 130, 132 may be circumscribed by the sheath 102. In exemplary form, each of the guides 130, 132 defines a hollow conduit extending therethrough, thereby sized to allow repositioning of one or more wires 140, 142, 144 extending therethrough or thereabout.

The wires 140, 142, 144 of the basket 104 may be operatively coupled to the line(s) 108 to facilitate repositioning of the basket between a closed or retracted position to an open or expanded position. In exemplary form, each wires 140, 142, 144 may comprises a single wire or multiple wire strands that are capable of being repositioned and optionally elastically deformed. By ways of example, the wires 140, 142, 144 may comprise a metal, a metal alloy, a polymer, or a polymer alloy, and, optionally, be shape set to embody a curved (non-linear) form. An exemplary metal alloy that may be used to fabricate the wires 140, 142, 144 includes, without limitation, nitinol. The wire or wire strands may embody a uniform cross-section along a longitudinal length or may have a cross-section that varies along a longitudinal length. The cross-section of the wire or wire strands may be circular, oblong, semicircular, triangular, rectangular, star shaped, or any other cross-section. By way of further example, the wires 140, 142, 144 may comprise a single strand of nitinol having a uniform circular cross-section and an outside diameter ranging between 0.0001 inches and 0.05 inches, such as 0.003 inches. By way of further example, each of the wires may have an overall length that is more than twice the longitudinal dominant dimension of a guide 130, 132.

In this exemplary embodiment, the basket 104 includes three wires 140, 142, 144 that each form a loop that is repositionable with respect to the sheath 102 to capture objects within an interior region defined by the loops. By way of example, the loops may be arranged in a triangular configuration. By way of example, the first and second wires 140, 142 may be joined to one another at a location 154 (i.e., a joint) in a fixed relationship. This fixed relationship may be the result of welding, gluing, soldering, twisting, weaving, or any other means to preclude longitudinal repositioning of the first and second wires 140, 142 at the joint 154. Alternatively, the first and second wires 140, 142 may comprise an integral single wire upstream from the joint 154 and split off downstream of the joint 154 to form the two separate wires 140, 142. In any event, the upstream portions of the first and second wires 140, 142 are operatively coupled to an anchor 158 associated with at least one of the sheath 102 or a guide 130, 132. As used with respect to this first exemplary extraction device 100, "upstream" refers to portions of the first and second wires 140, 142 between the joint 154 and the anchor 158, where the anchor retains the first and second wires in a fixed location.

The downstream portions of the first and second wires 140, 142 may extend into respective ones of the guides 130, 132. In exemplary form, the downstream portions of the first and second wires 140, 142 may be freely repositionable along or within a respective guide 130, 132, or one downstream portion of either the first and second wire 140, 142 may be stationary with respect to a guide 130, 132 (e.g., such as being mounted to the anchor location 158) while the second downstream portion of the other wire 140, 142 is freely repositionable and operatively coupled to the line 108. In this fashion, the downstream portions of the first and second wires 140, 142 exposed from the distal ends of the guides 130, 132 are operative to form the first and second loops. As used with respect to this first exemplary extraction device 100, "downstream" refers to portions of the first and second wires 140, 142 between the joint 154 and where the wires are operatively coupled to the line 108.

A third of the wires 144 may also be operatively coupled to the line 108 and may be operatively coupled to the anchor 158 at an opposing end. In exemplary form, the third wire 144 may form a third loop. By way of example, opposing portions of the third wire 144 extend through or along respective ones of the guides 130, 132. In a case where the first and second wires 140, 142 are freely repositionable within a respective guide 130, 132, at least one portion of the third wire 144 may be fixedly mounted to the anchor 158, while another portion of the third wire may be freely repositionable along or within at least one of the guides 130, 132. As a result, one guide 130 may accommodate two or more wires 140, 144 that are freely repositionable along or within that guide, while the other guide 132 may have a wire 142 freely repositionable with respect thereto and a second wire 142 not freely repositionable with respect thereto. In exemplary form, the wire 144 fixedly mounted to the anchor 158 may be secured thereto using adhesive 160 or any other means of bonding or retention such as, without limitation, welding and brazing. As referenced previously, the line 108 may be operatively coupled to at least two of the three wires 140, 142, 144 so that an operator can utilize the handle control 106 to reposition the basket 104 between a fully retracted position and a fully expanded position. By way of example, the line 108 may comprise any number of materials and constructions such as, without limitation, metals, metal alloys, single wire, multiple wires, whether in parallel, twisted, or braided. In exemplary form, the line 108 comprises a nitinol single wire having a circular cross-section and having a diameter of approximately 0.015 inches. It should be noted, however, that the diameter of the line 108 may be proportional or sized in relation to the size of the sheath 102 so that larger sheath diameters can accommodate larger line diameters and, vice versa, smaller sheath diameters can accommodate smaller line diameters.

In exemplary form, the handle control 106 comprises complementary housing halves 202, 204 mounted to one another that may be fixedly or repositionably mounted to the sheath 102. These housing halves 202, 204 delineate an interior region within which a first actuator 210 may be repositioned. The first actuator 210 may extend through an opening 212 within at least one of the halves 202, 204 (the halves 202, 204 may also cooperate to delineate the opening 212) and may be operatively coupled to the line 108. In this fashion, repositioning of the actuator 210 may cause longitudinal repositioning of the line 108 with respect to the sheath 102.

It is also within the scope of the disclosure to operatively couple the line 108 to the housing halves 202, 204, rather than to the first actuator 210, where the housing halves are repositionable with respect to the sheath 102 and may be spring biased with respect thereto so as to provide either a biased open or biased closed basket position. In such a circumstance, the first actuator 210 may be operatively coupled to the sheath 102. Accordingly, longitudinal motion of the housing halves 202, 204 with respect to the sheath 102 is operative to transmit corresponding longitudinal motion to the line 108 with respect to the sheath 102. And this longitudinal motion of the line 108 is correspondingly carried over into motion of at least two of the three wires 140, 142, 144 (and optionally all three wires) to open and close the basket 104.

In either exemplary control discussed immediately above, travel of the first actuator 210 or housing halves 202, 204 relative to the sheath 102 may be limited so that this range of motion/travel corresponds with the range of travel between fully extending and fully retracting (i.e., opening and closing) the basket 104. In other words, when the first actuator 210 or housing halves 202, 204 is at one end of its range of motion relative to the sheath 102, the basket 104 may be fully retracted, whereas the basket may be fully extended when the first actuator or housing halves is at its opposite end of its range of motion relative to the sheath. Consequently, repositioning of the first actuator 210 or the housing halves 202, 204 relative to the sheath 102 is operative to manipulate the relative shape of the basket 104 by repositioning the basket between a fully retracted position and a fully expanded position.

Figure 11:
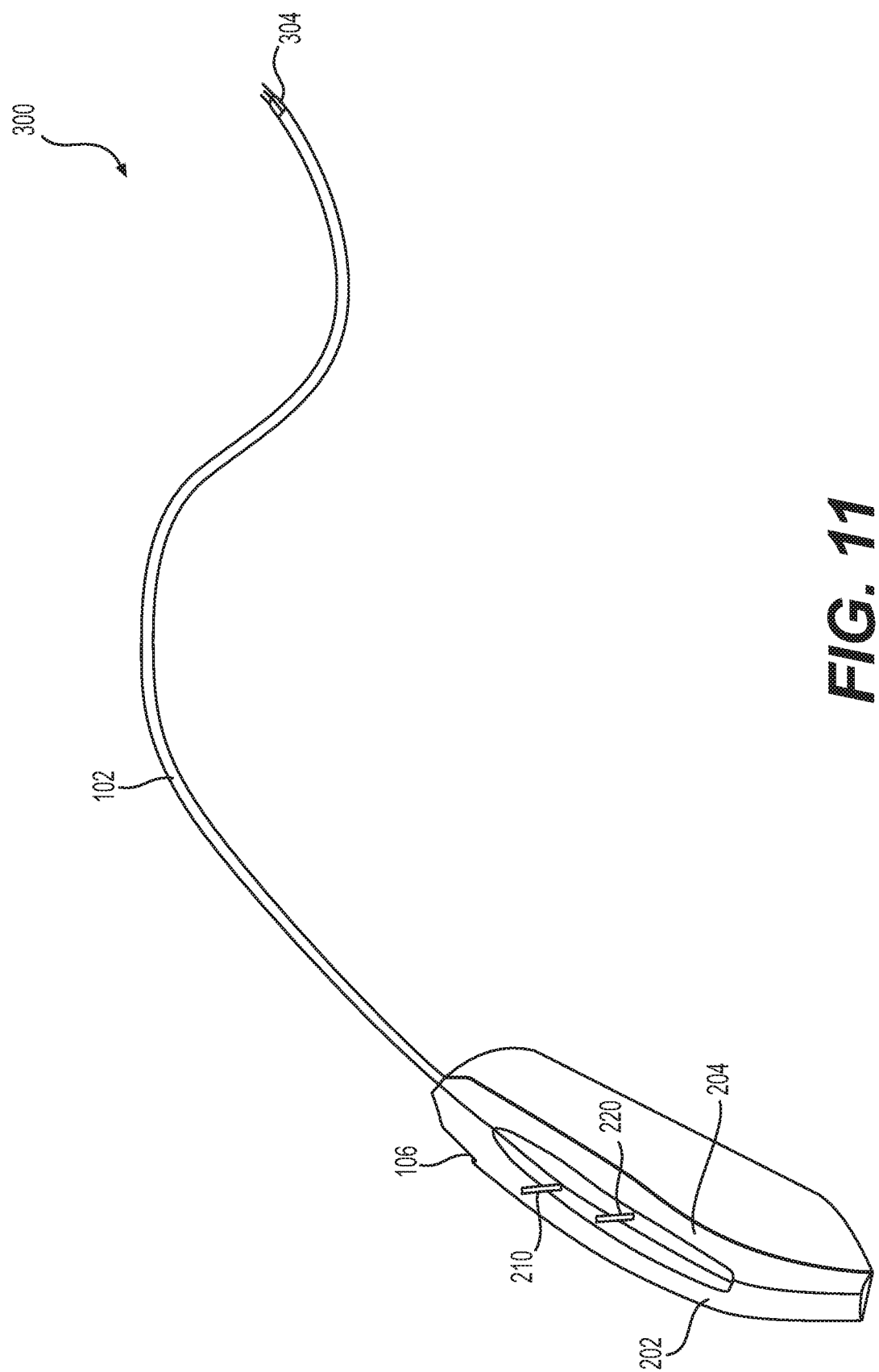
FIG. 11 is an elevated perspective view of a second exemplary medical extraction device in accordance with the instant disclosure.

Turning to FIG. 11, though not required, the handle control 106 may include a second actuator 220 that is also repositionable with respect to the housing halves 202, 204. In a circumstance where one or more of the guides 130, 132 are not rigidly mounted to the sheath 102, and can be longitudinally repositionable with respect to the sheath, the second actuator 220 may be operatively coupled to a hollow conduit 230 that extends along an interior of the sheath. In exemplary form, the conduit 230 may have an external axial dominant dimension that is smaller than the smallest internal axial dominant dimension of the sheath 102, thereby allowing the conduit to be longitudinally repositionable with respect to the sheath. Moreover, the conduit 230 may have a continuous internal cavity that extends longitudinally through which the line(s) 108 may extend. In such a circumstance, the line(s) 108 may be independently longitudinally repositionable with respect to the conduit 230 and the sheath 102. Similarly, the conduit 230 may be independently longitudinally repositionable with respect to the line(s) 108 and the sheath 102. In this fashion, longitudinal motion of the second actuator 220 with respect to the halves 202, 204 may be operative to transmit corresponding longitudinal motion to the conduit 230 within the sheath 102. And this longitudinal motion of the conduit 230 may be correspondingly carried over into motion of the guides 130, 132 to extend and retract the guides with respect to the sheath 102. In this exemplary embodiment, travel of the second actuator 220 may be limited so that its range of motion corresponds with the range of extending and retracting of the guides 130, 132 with respect to the sheath 102. In other words, when the second actuator 220 is at one end of its range of motion, the guides 130, 132 may be fully retracted within the sheath 102, whereas the guides 130, 132 may be fully (or near fully) extended out of the sheath 102 when the second actuator is at an opposite end of its range of motion. Consequently, repositioning of the second actuator 220 with respect to the housing halves 202, 204 may be operative to manipulate the relative shape of the basket 104.

Referring specifically to FIGS. 1, 7-10, 22-24 and 29, the foregoing first medical extraction device 100 may be utilized to extract various objects from within an interior of an anatomical cavity. By way of exemplary explanation, use of the extraction device 100 will be explained in the context of a renal kidney stone removal procedure. Nevertheless, those skilled in the art will understand that use of the medical extraction device 100 shall not be limited to renal kidney stone removal procedures, but rather that this description is just one of numerous procedures for which the extraction device 100 has application.

Figure 7:
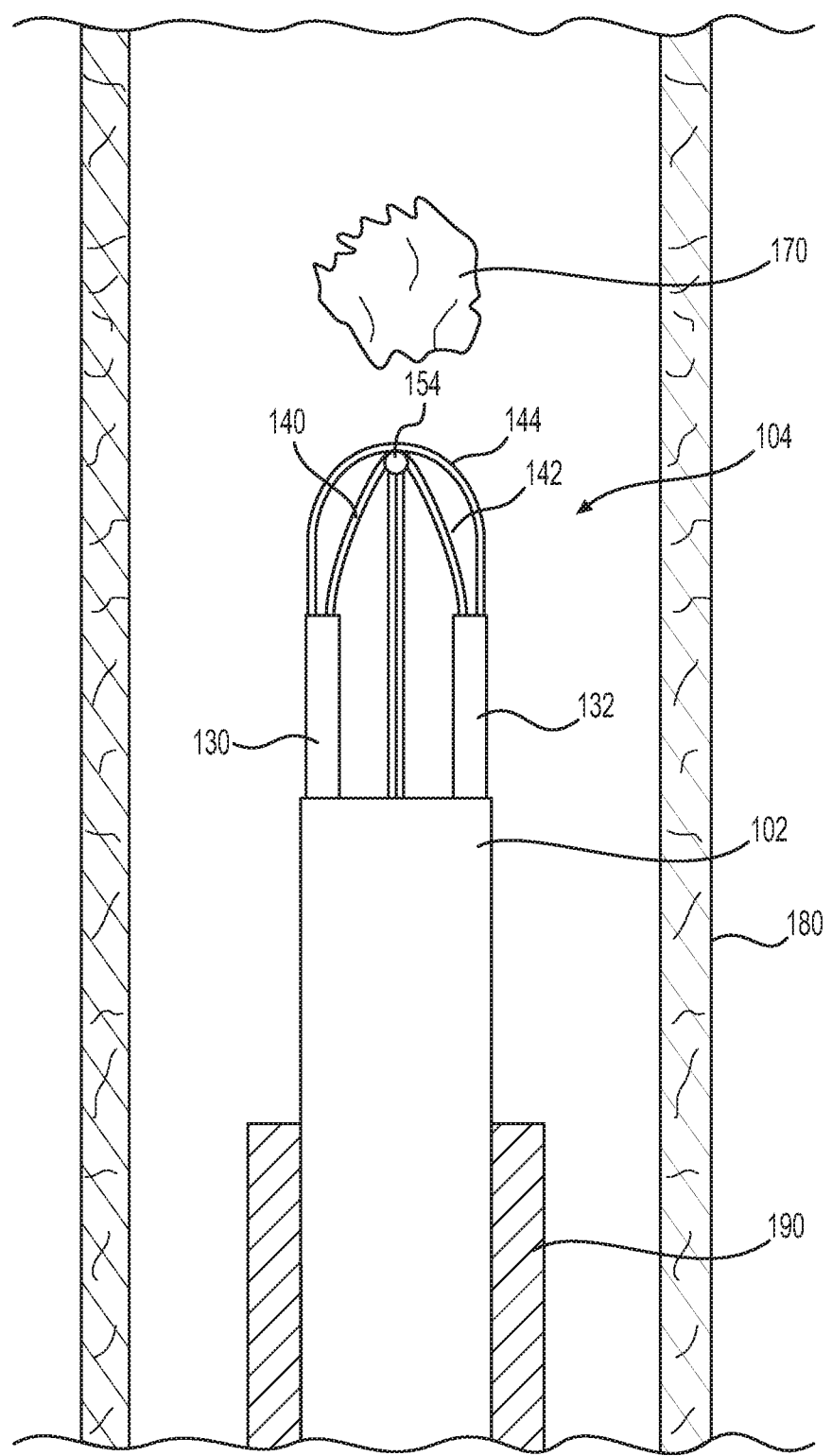
FIG. 7 is a profile view of a distal end of the first exemplary medical extraction device extending through a ureteroscope within a renal path just prior to the basket reaching an object to be removed.
Figure 23:
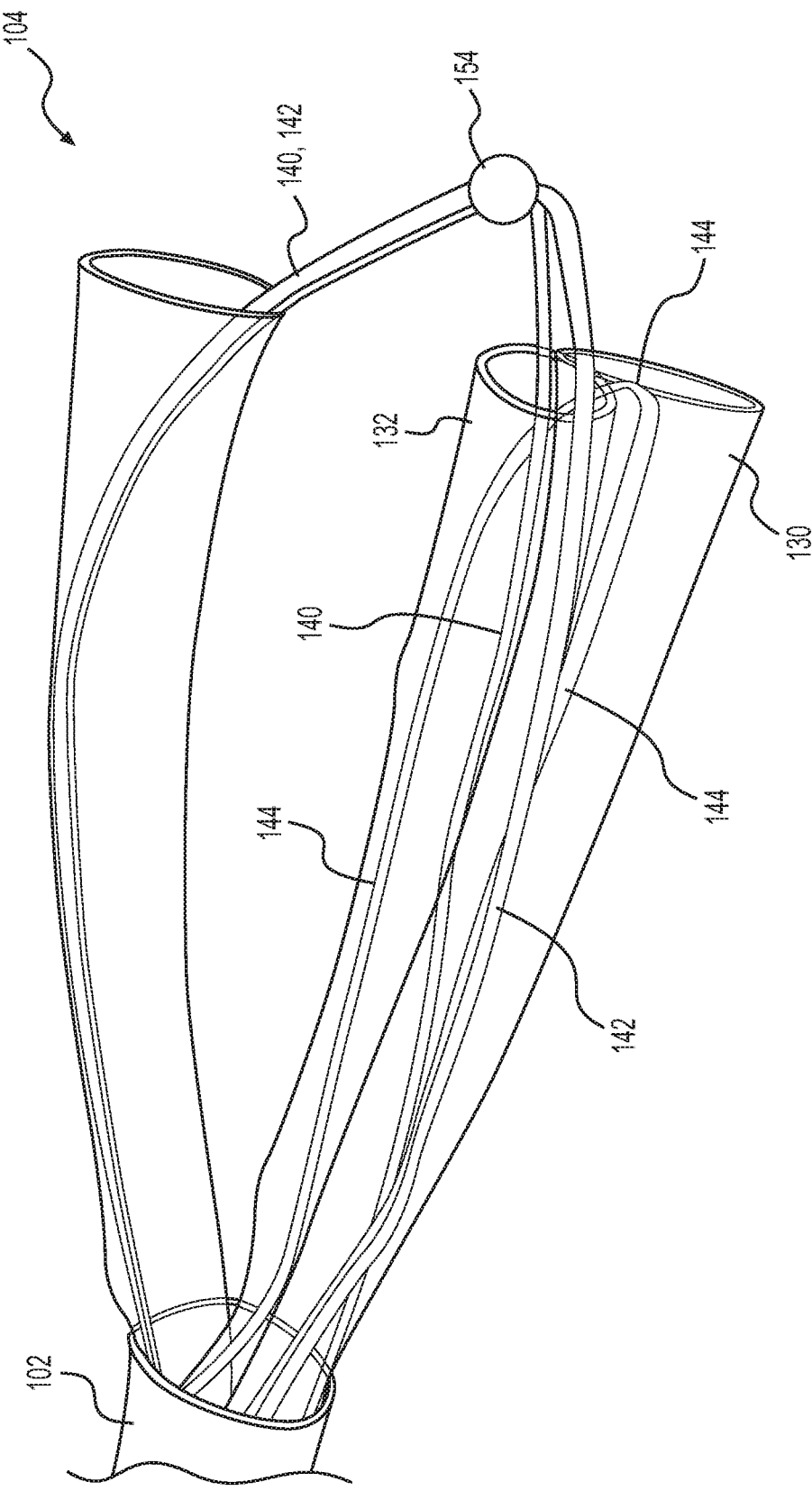
FIG. 23 is an elevated perspective view of the basket of the first exemplary medical extraction device of FIG. 1 in a closed or retracted position.

Initially, a suitable renal path 180 to the kidney in the patient's body may be explored and appropriate visualization may also be provided by means of a scope 190 (e.g., ureteroscope) traversing the renal path. Upon approximating the location of a target object 170 (e.g., a kidney stone), the basket 104 end of the extraction device 100, coupled to the sheath 102, may be advanced through the scope 190 while the basket is in a retracted position, as shown in FIGS. 7 and 23, to advance the basket and distal end of the sheath beyond a distal end of the scope 190. Continued advancing of the sheath 102 and basket 104 may continue until the basket 104 reaches the targeted area where the object 170 to be removed is located. After the basket 104 reaches the desired area as determined by visual inspection of the scope 190, an operator may grasp the handle control 106 (i.e., complementary housing halves 202, 204) and repositions one or both of the actuators 210, 220 relative to the housing halves 202, 204 (or reposition the handle housings with respect to the sheath) to reposition the line 108 relative to the sheath 102, thereby repositioning the basket from its retracted position toward an open position.

Figure 8:
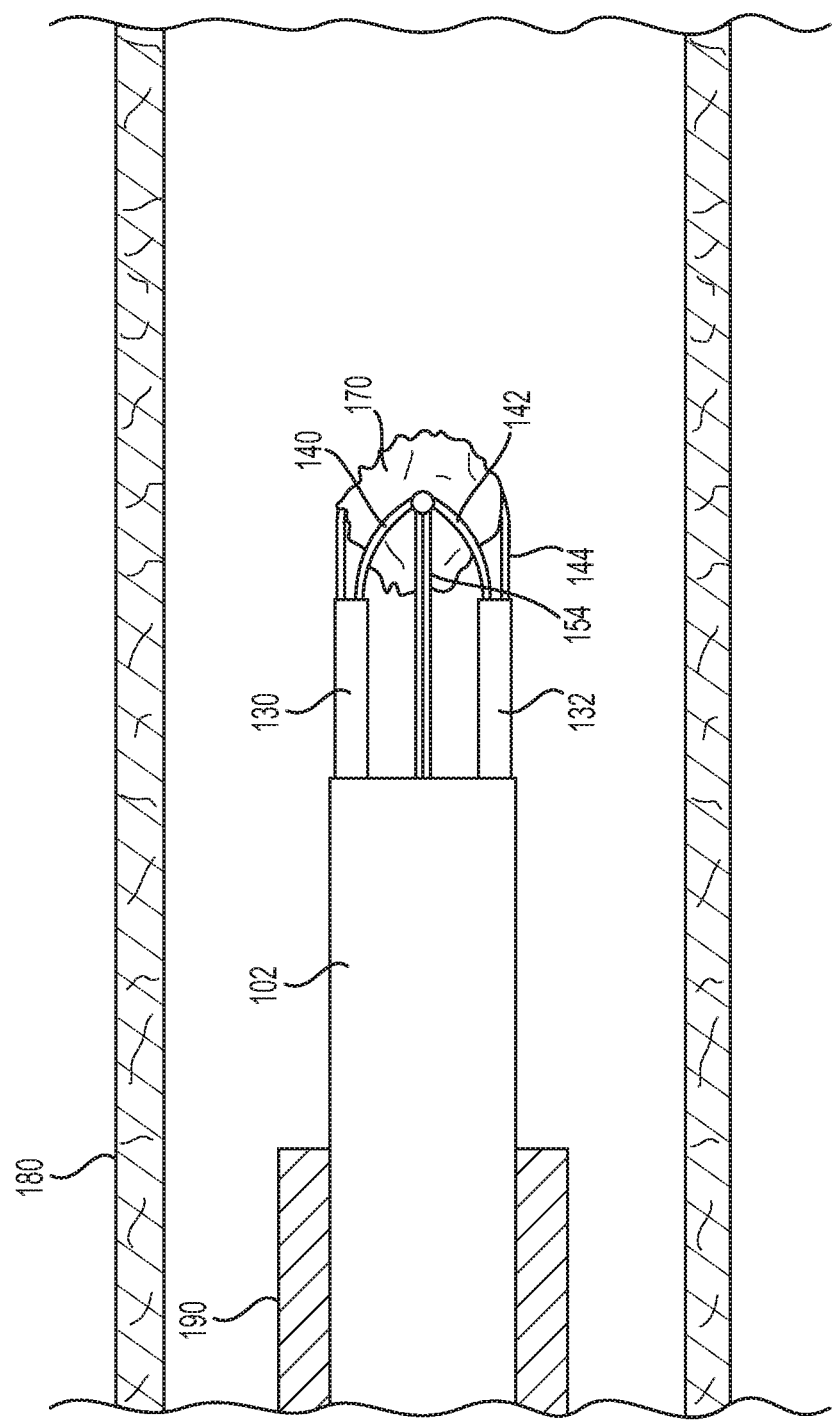
FIG. 8 is a profile view of the distal end of the first exemplary medical extraction device extending through a ureteroscope within a renal path with the basket open to receive the object to be removed.

In a circumstance where the handle control 106 includes a second actuator 220, the second actuator and the first actuator 210 may be concurrently repositioned or repositioned independent of one another to move the basket from a closed or retracted position to an open or expanded position. In exemplary form, the second actuator 220 may be repositioned distally (toward the basket 104 and with respect to the handle housings 202, 204), thereby causing the conduit 230 to move longitudinally through the sheath 102 and direct the guides 130, 132 to extend beyond (or further beyond) the sheath. The operator of the handle control 106 may then reposition the first actuator 210 distally (toward the basket 104 and with respect to the handle housings 202, 204), thereby causing the line 108 to move longitudinally through the sheath 102 and cause the wire 140, 144 length extending beyond the guides 130, 132 to increase as well as increasing the wire 142 length. FIGS. 7 and 8 depict an exemplary position of the basket 104 where the guides 130, 132 are at least partially extended from the sheath 102 (via the second actuator 220, or by default if not actuated) and the wires 140, 142, 144 are at least partially extended, which coincides with a partially open or fully open (i.e., expanded) position. This open or expanded position may be maintained while the entire distal portion of the extraction device 100 is repositioned so that the target object 170 intending to be captured (e.g., a kidney stone) may be received within the open basket 104, as shown in FIG. 8.

Figure 9:
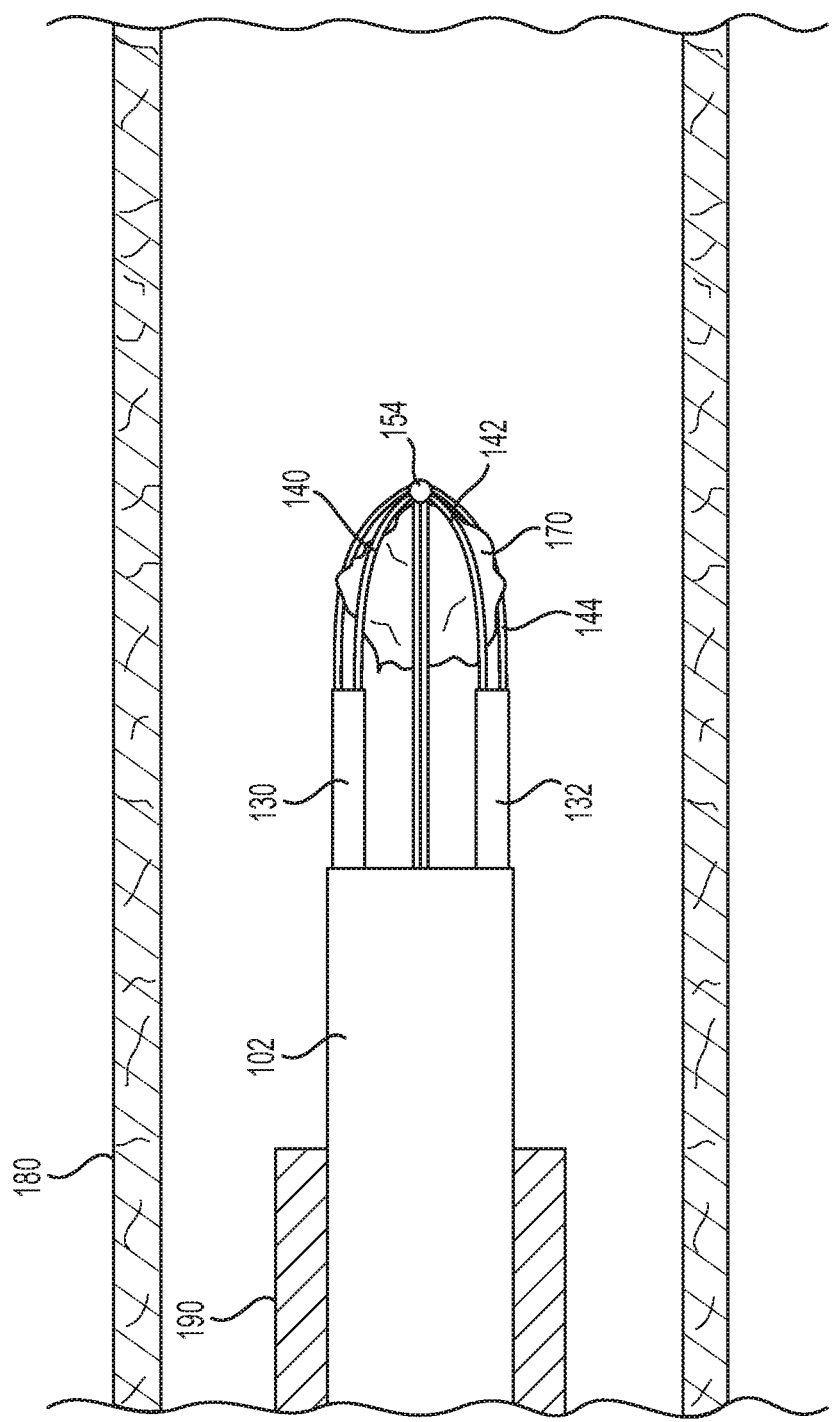
FIG. 9 is a profile view of the distal end of the first exemplary medical extraction device extending through a ureteroscope within a renal path with the basket repositioned to an encompassing position to surround the object to be removed.
Figure 10:
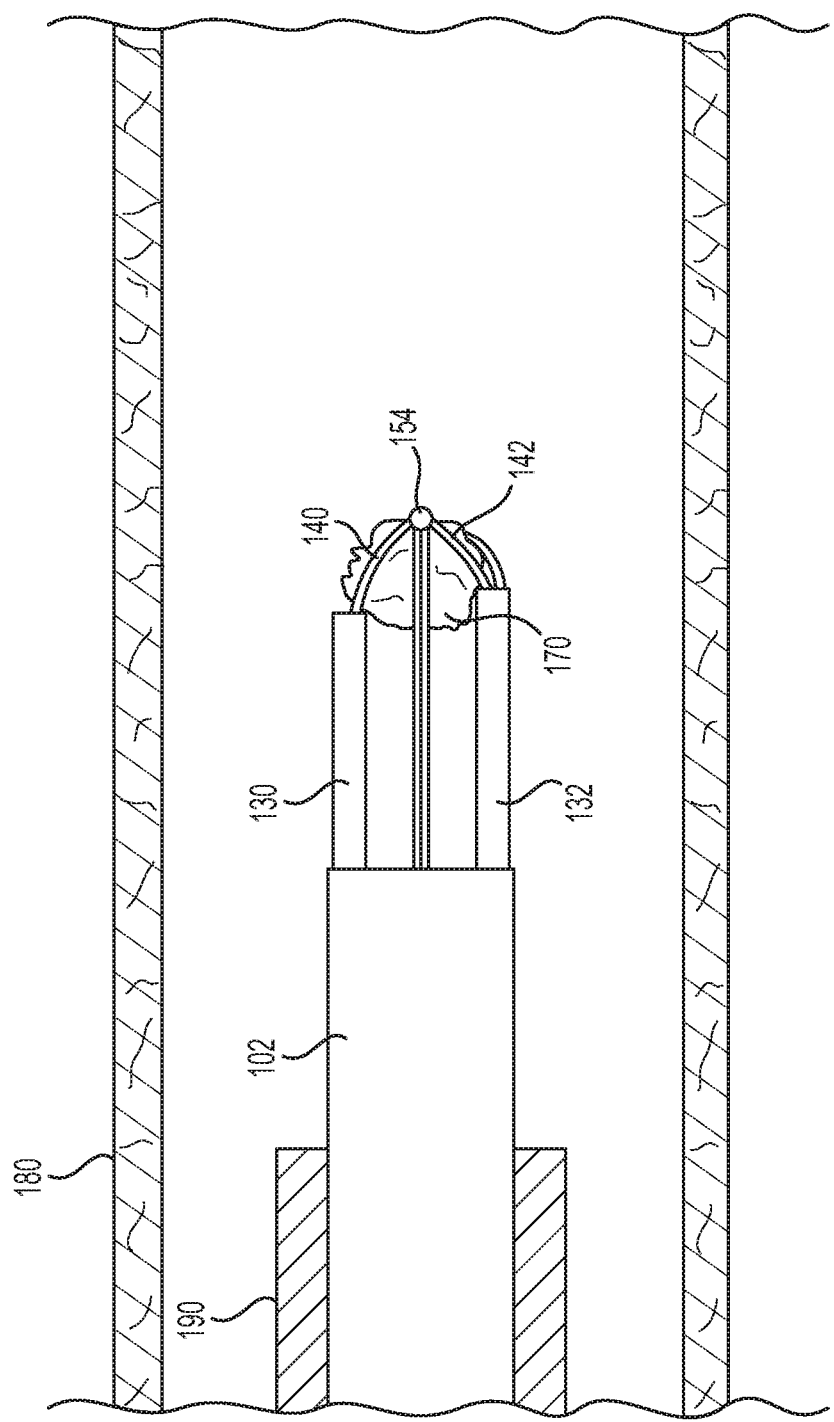
FIG. 10 is a profile view of the distal end of the first exemplary medical extraction device extending through a ureteroscope within a renal path with the basket repositioned to an encompassing position to surround the object to be removed, as well as showing an optional repositioning of the guides in closer proximity to the object to be removed just prior to object removal.
Figure 24:
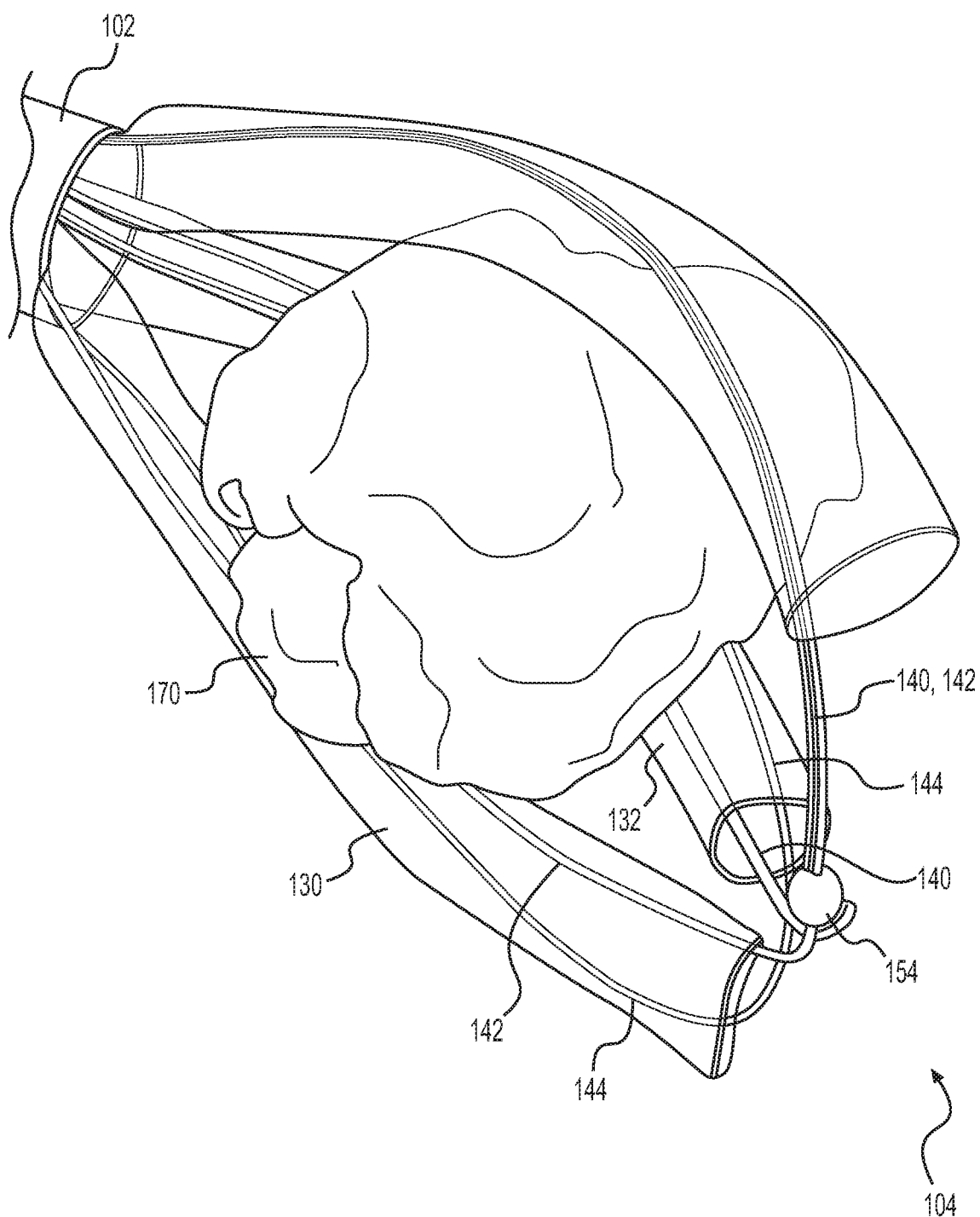
FIG. 24 is an elevated perspective view of the basket of the first exemplary medical extraction device of FIG. 1 in a closed or retracted position, but with an object captured by the basket.
Figure 29:
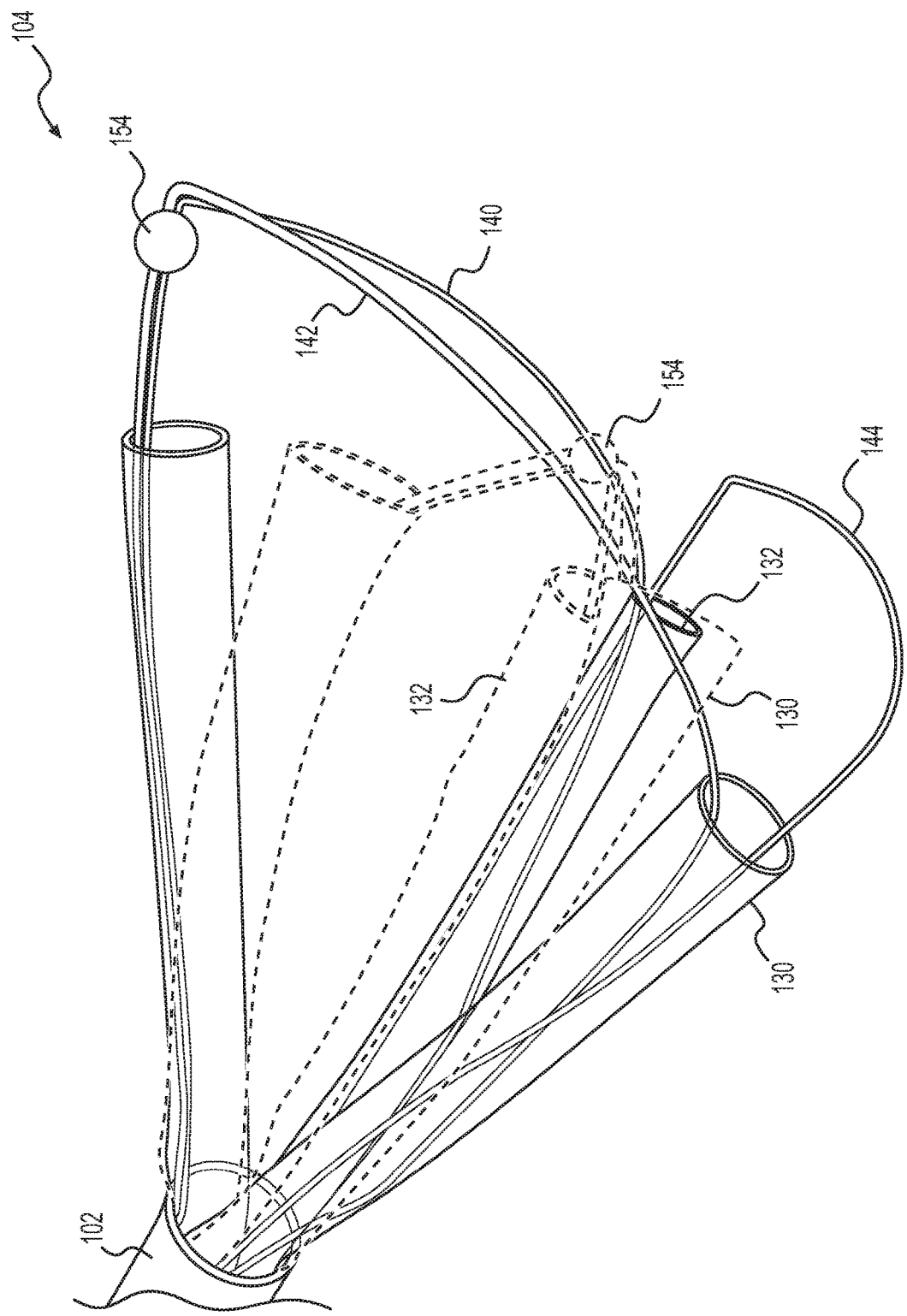
FIG. 29 is an elevated perspective view of the basket of the first exemplary medical extraction device of FIG. 1 in an open or expanded position, as well as showing in phantom the same exemplary basket in a closed or retracted position.
Figure 30:
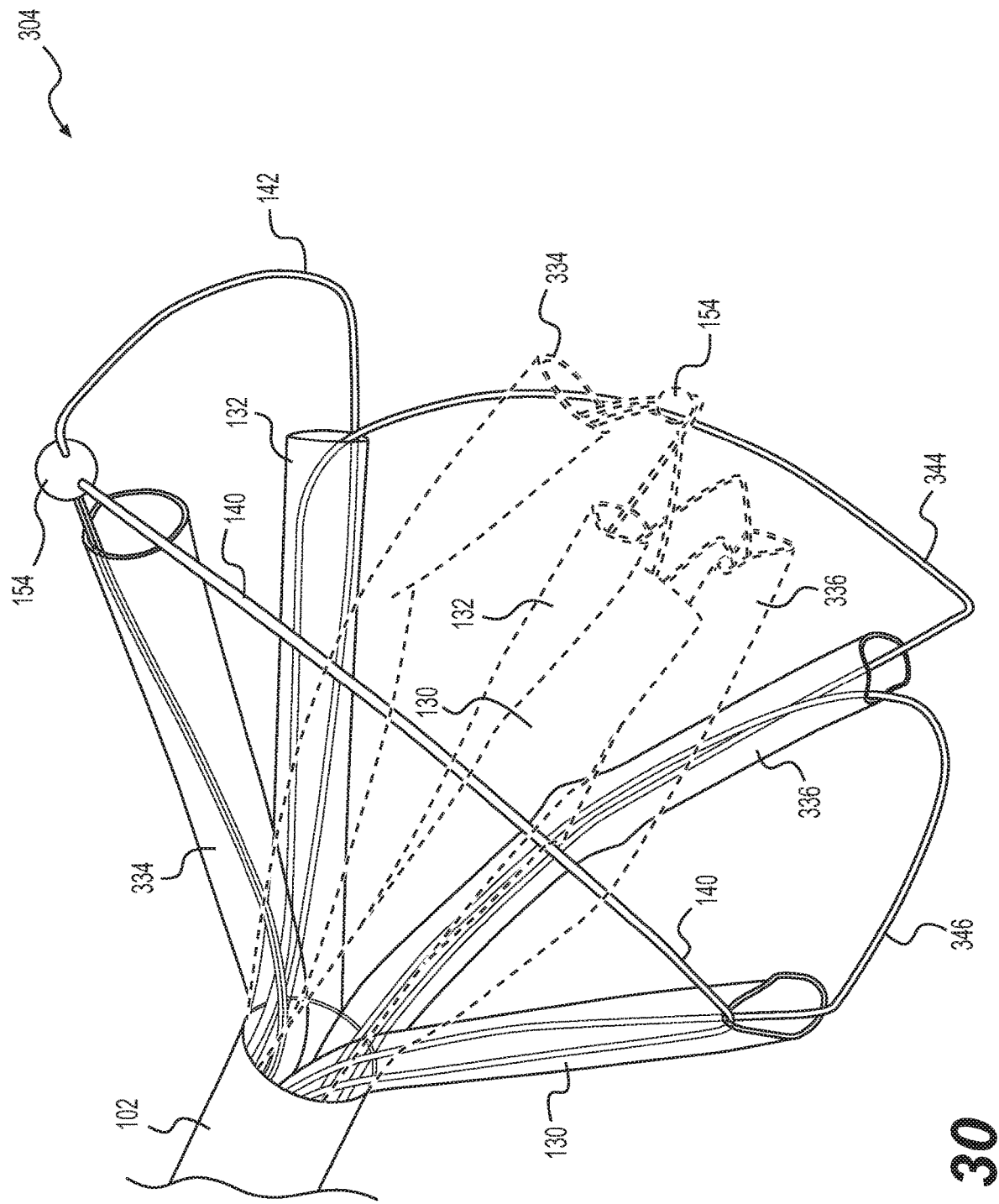
FIG. 30 is an elevated perspective view of the basket of the second exemplary medical extraction device of FIG. 11 in an open or expanded position, as well as showing in phantom the same exemplary basket in a closed or retracted position.

After the target object 170 is at least partially received within the open basket 104, the first actuator 210 may be repositioned proximally (away from the basket 104 and with respect to the handle housings 202, 204), thereby causing the line 108 to move longitudinally through the sheath 102 and causing the wire lengths 140, 142, 144 extending beyond the guides 130, 132 to decrease as well as decreasing the wire length associated with the loops. This decreased length of the wires 140, 144 coincides with the joint 154 comprising a tip that arches over and moves in an arcuate path to come behind the target object 170, which creates a backstop to preclude the object from backing out of the basket, as shown in FIGS. 9, 24, and 29. Depending upon the size of the target object 170 and the operator's confidence as to whether the object will stay within the basket 104 upon relocating the entire distal portion of the extraction device 100 proximally (for eventual removal of the basket 104 and object 170 from the renal path 180, for example), the operator may reposition the second actuator 220 distally (toward the basket 104 and with respect to the handle housings 202, 204), thereby causing the guides 130, 132 to move further longitudinally through the sheath 102 and cause the wire 140, 142, 144 lengths extending beyond the guides 130, 132 to decrease as well as decreasing the wire length associated with the loops, thereby tightening the loops around the target object, as depicted in FIG. 10. Post capturing the target object 170 within the basket 104, the extraction device 100 and object 170 may be removed from the renal path 180.

Figure 22:
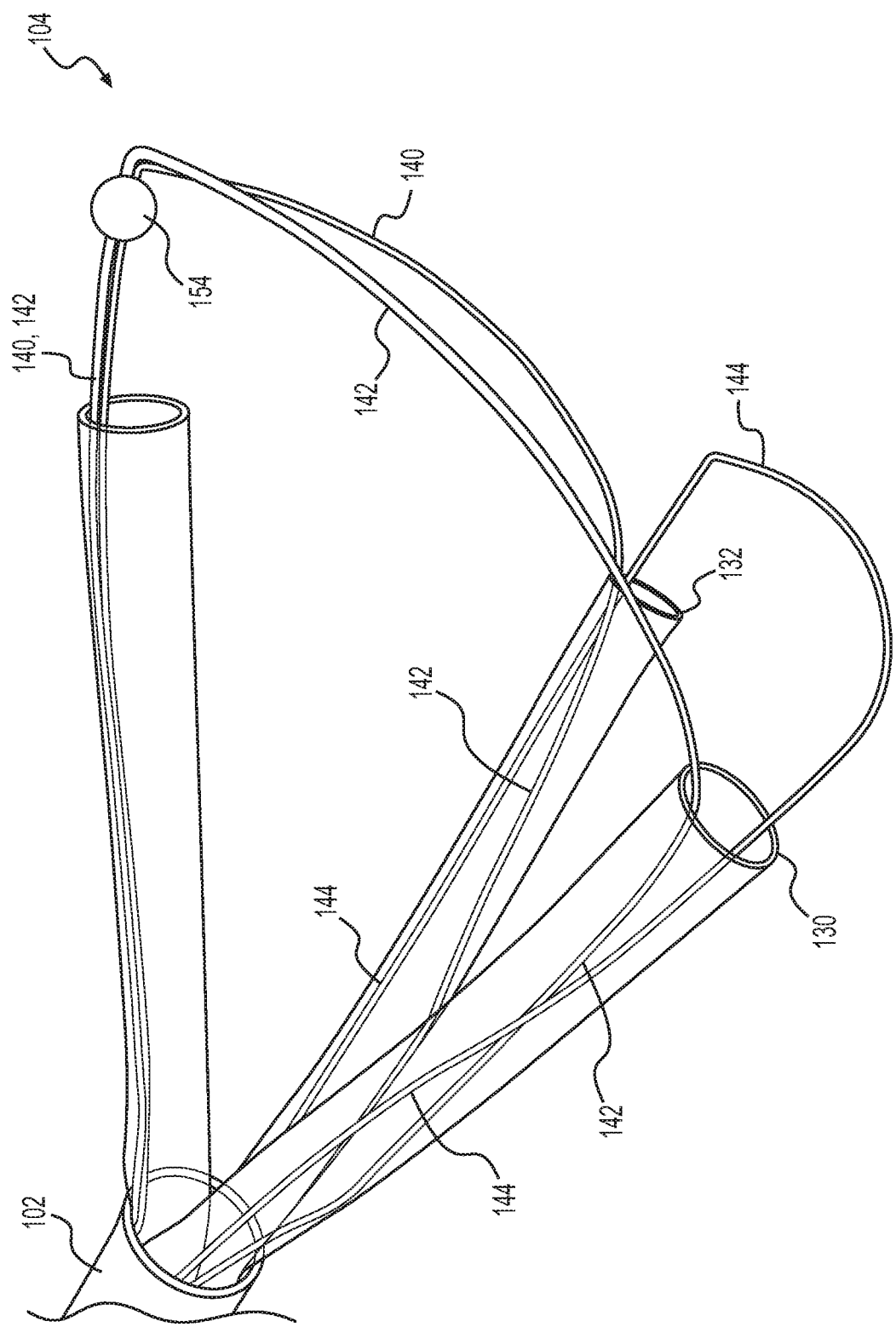
FIG. 22 is an elevated perspective view of the basket of the first exemplary medical extraction device of FIG. 1 in an open or expanded position.

Alternatively, in a circumstance where the guides 130, 132 are not repositionable with respect to the sheath 102, the first actuator 210 may be repositioned to move the basket from a closed or retracted position to an open or expanded position upon reaching the target object 170. In exemplary form, the operator of the handle control 106 may reposition the first actuator 210 distally (toward the basket 104), thereby causing the line 108 to move longitudinally through the sheath 102 and cause the wire 140, 144 lengths extending beyond the guides 130, 132 to increase as well as increasing the wire 142 length, thereby increasing the length of each of the three loops extending from the sheath. FIGS. 7, 8, and 22 depict an exemplary an open or expanded position of the basket 104 where the guides 130, 132 are partially extended from the sheath 102 and the wires 140, 142, 144 are partially extended from the guides and sheath. This open or expanded position may be maintained while the entire distal portion of the extraction device 100 is repositioned further distally so that the target object 170 to be captured (e.g., a kidney stone) may be received within the open basket 104, as shown in FIG. 8. After the target object 170 is at least partially received within the open basket 104, the first actuator 210 may be repositioned proximally (away from the basket 104), thereby causing the line 108 to move longitudinally through the sheath 102 and causing the wire 140, 142, 144 lengths extending beyond the guides 130, 132 to decrease and correspondingly decrease the length of the loops extending beyond the guides. This decreased length of the wires 140, 142, 144 coincides with the joint 154 comprising a tip that arches over and moves in an arcuate path to come behind the target object 170, which creates a backstop to preclude the object from backing out of the basket 104, as shown in FIGS. 9, 23, and 29. After the joint 154 has been repositioned behind the target object 170, the extraction device 100 and target object 170 may be removed from the renal path 180.

Referencing FIGS. 11-20, 25-28, and 30, a second exemplary embodiment of a medical extraction device 300 includes an elongated hollow sheath 102 from which extends at a distal end of thereof a repositionable basket 304. As used herein, reference numerals in common with the first exemplary embodiment refer to elements that are the same or insubstantially different from those of the first exemplary embodiment. Accordingly, for purposes of brevity, a discussion of the elements in common between the two embodiments has been omitted.

The basket 304 is operatively connected to a handle control 106 via a line 108 (that may comprise one or multiple lines), which extends through the hollow portion of the sheath and is longitudinally repositionable with respect to the sheath, to facilitate opening (i.e., an expanded position) and closing (i.e., a retracted position) of the basket. A proximal aspect of the sheath 102 may be fixed or repositionably mounted to the handle control 106.

Figure 12:
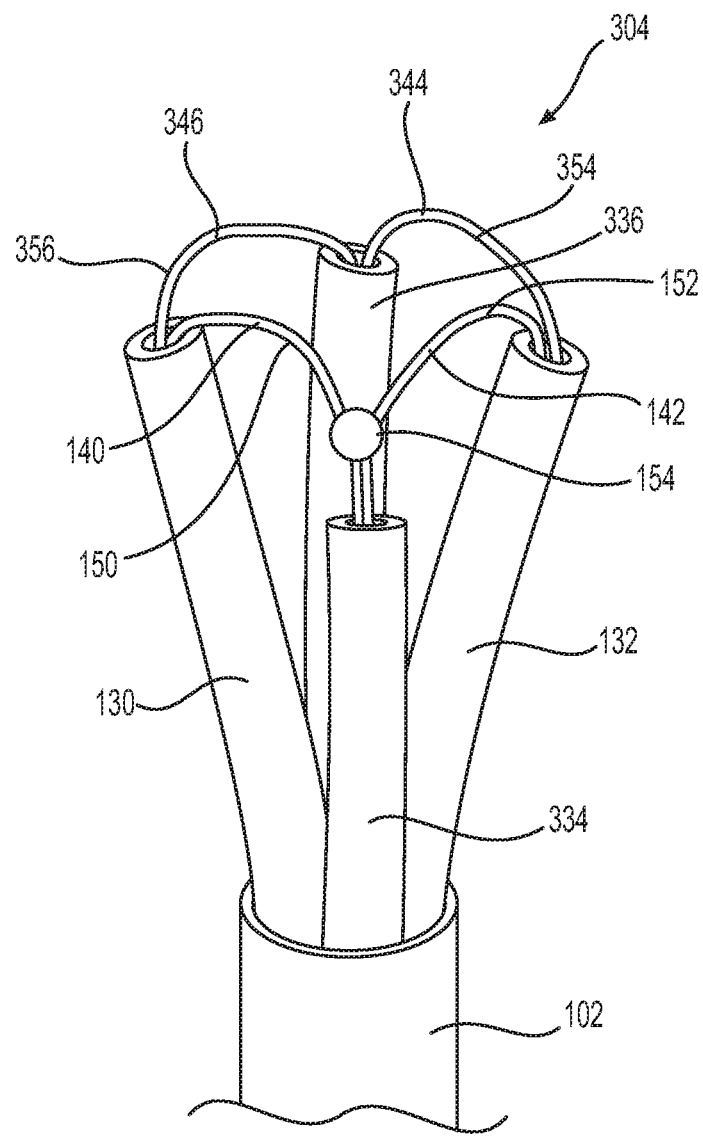
FIG. 12 is an isolated perspective view of a distal end of the second exemplary medical extraction device of FIG. 11 showing a basket extending beyond a sheath.
Figure 13:
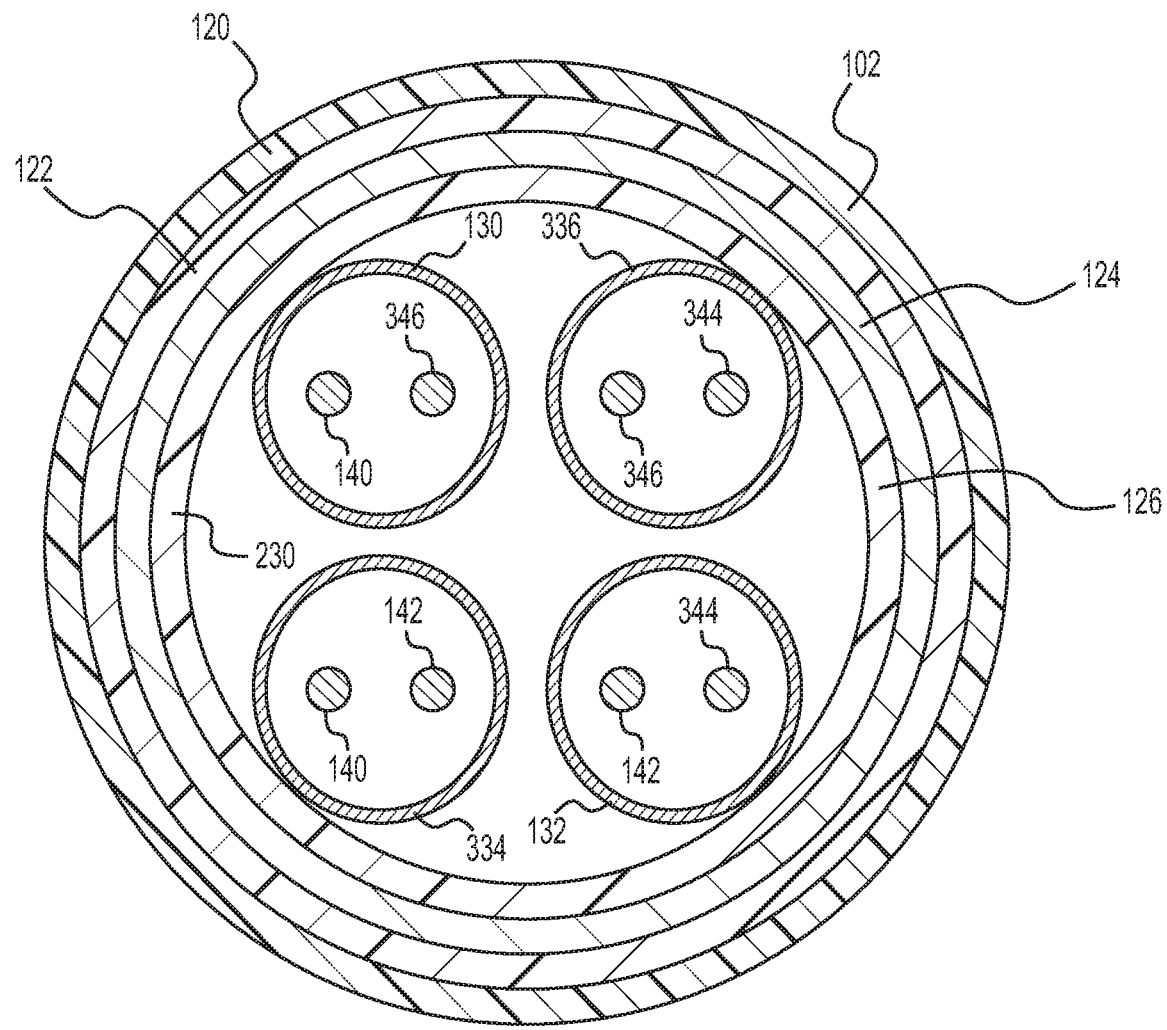
FIG. 13 is a cross-sectional view of exemplary components extending through a sheath taken just prior to a distal end of the sheath that shows the respective wires and guides where the guides are fixed relative to the sheath of the second exemplary medical extraction device.
Figure 14:
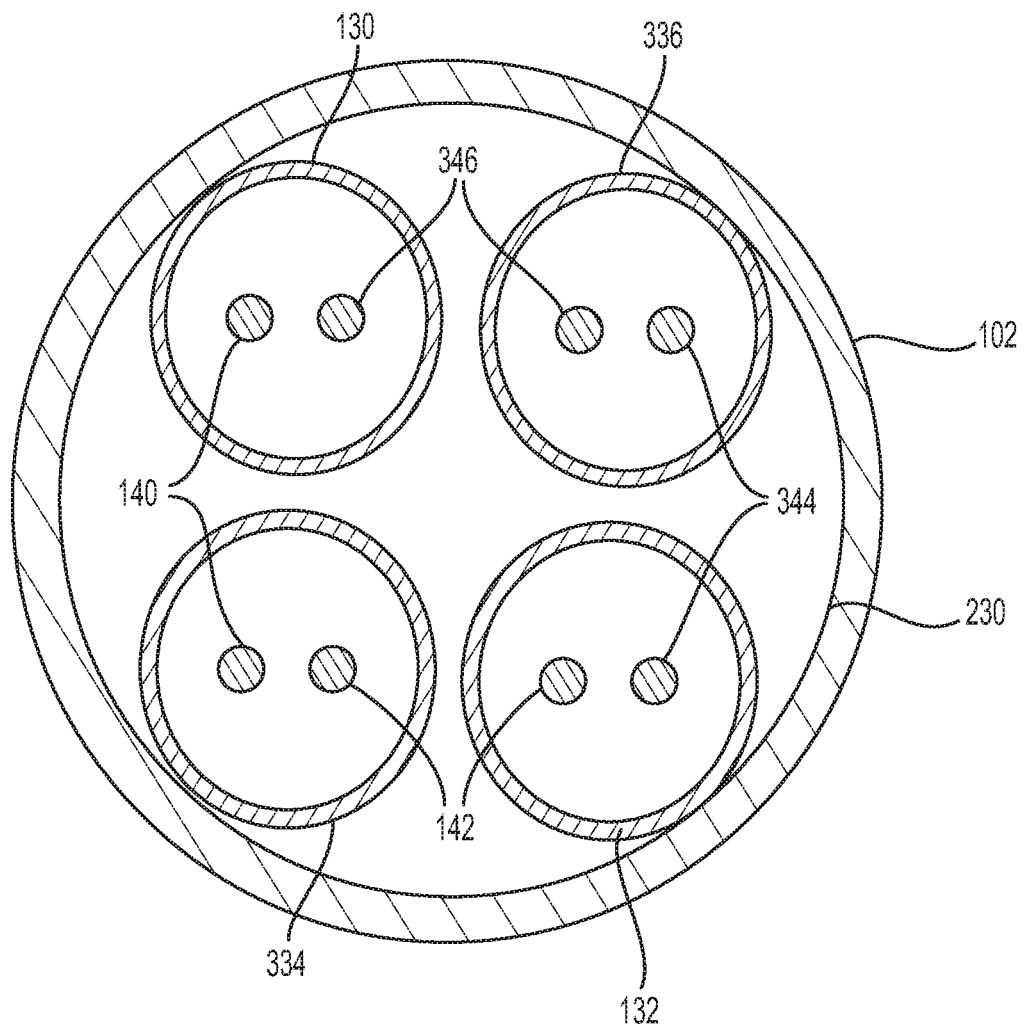
FIG. 14 is a cross-sectional view of exemplary components extending through a sheath taken just prior to a distal end of the sheath that shows the respective wires and guides where the guides are repositionable relative to the sheath of the second alternate exemplary medical extraction device.
Figure 15A:
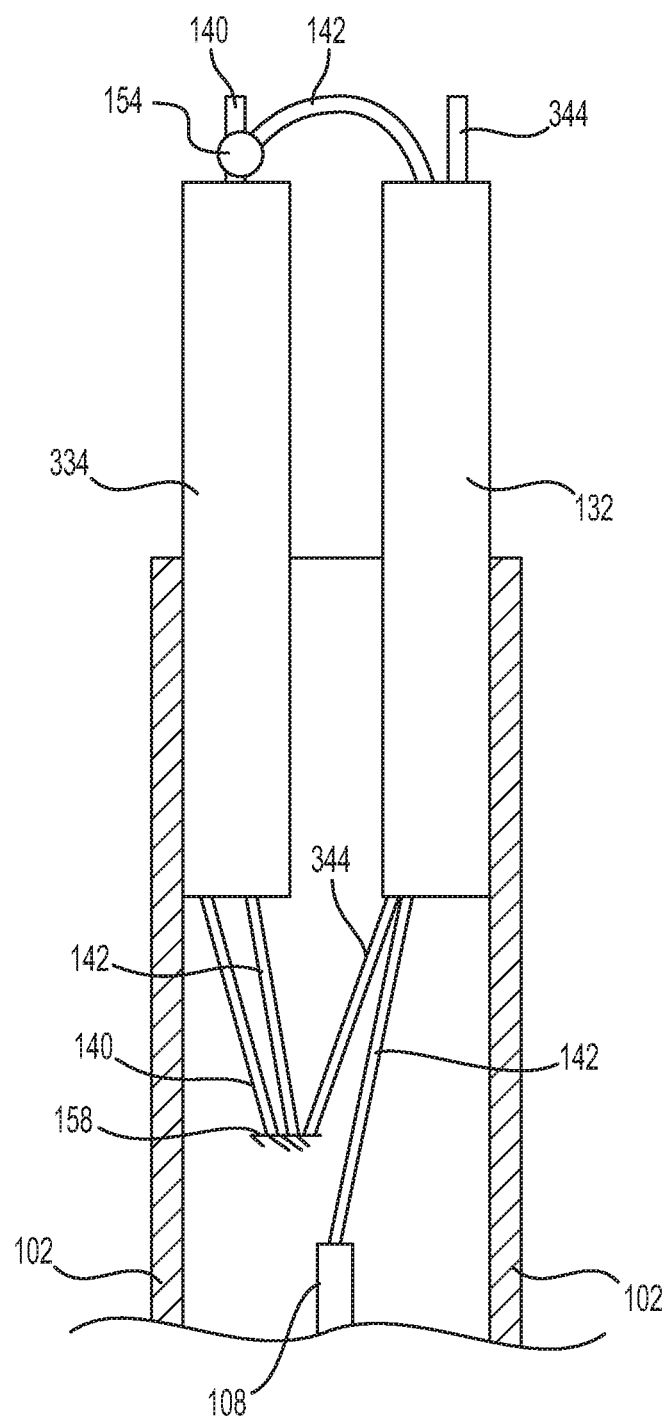
FIG. 15A is a cross-sectional view of an exemplary sheath and a perspective view of exemplary components extending through the sheath taken just prior to a distal end of the sheath that shows the respective wires and two guides where the guides are fixed relative to the sheath of the second exemplary medical extraction device.
Figure 15B:
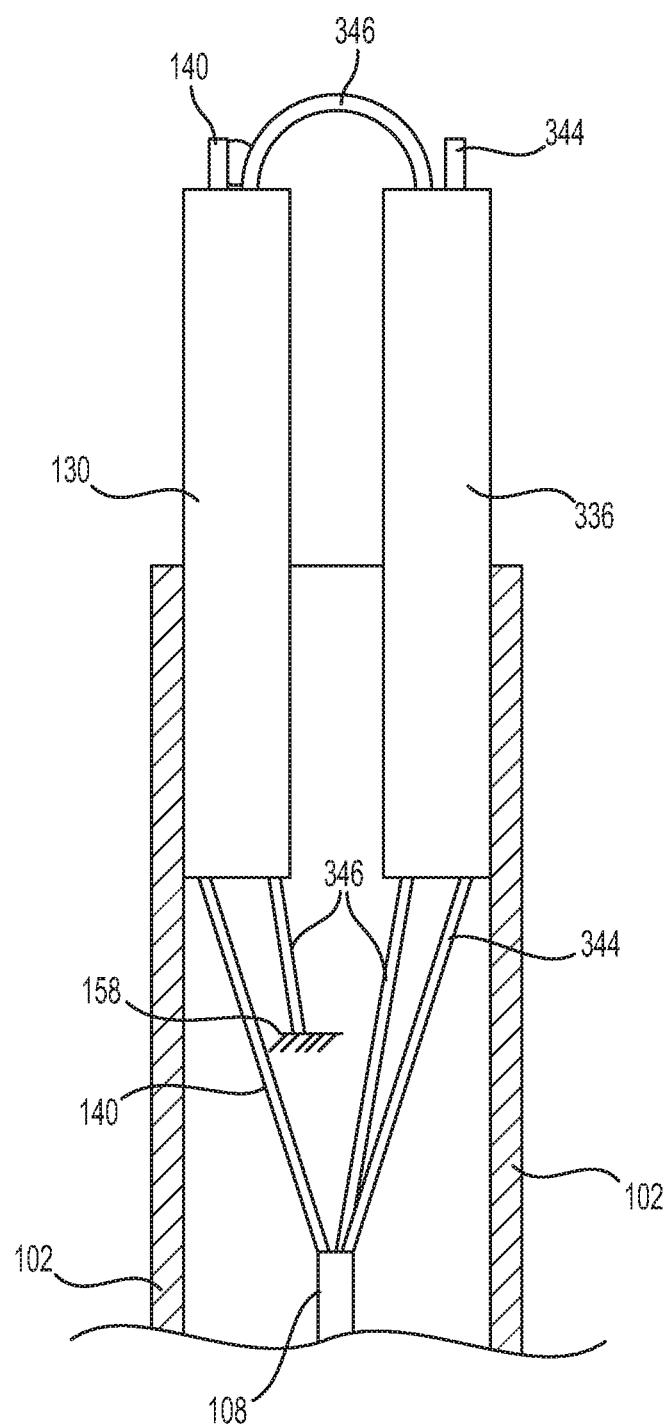
FIG. 15B is a cross-sectional view of the exemplary sheath and a perspective view of certain other exemplary components extending through the sheath of FIG. 15A taken just prior to the distal end of the sheath showing the respective wires and the other two guides where the guides are fixed relative to the sheath of the second exemplary medical extraction device.

By way of example, turning to FIG. 12, the basket 304 may comprise three or more guides 130, 132, 334, 336 through which each extends two or more wires 140, 142, 344, 346. For example, the guides 130, 132, 334, 336 may each be fabricated from a suitable plastic material such as, without limitation, polyethylene, polypropylene, polyester, polyvinyl chloride, polyimide or the like. But it should also be noted that the guides 130, 132, 334, 336 may be fabricated from materials other than plastics such as, without limitation, metals and metal alloys. The guides 130, 132, 334, 336 may be deformable and, alternatively, elastically deformable. Each of the guides 130, 132, 334, 336 may be fixedly secured to the sheath 102 (such as by way of adhesive 360 or other bonding means) or may be repositionable with respect to the sheath. By way of further example, at least a portion of the guides 130, 132, 334, 336 may be circumscribed by the sheath 102. In exemplary form, the guides 130, 132, 334, 336 define a respective hollow conduit extending therethrough, thereby sized to allow repositioning of one or more wires 140, 142, 344, 346 extending therethrough.

The wires 140, 142, 344, 346 of the basket 304 may be operatively coupled to the line(s) 108 to facilitate repositioning of the basket between a closed or retracted position and an open or extended position. In exemplary form, the wires 140, 142, 344, 346 may comprises a wire or strands of wire that are capable of being repositioned and optionally elastically deformed. By ways of example, the wires 140, 142, 344, 346 may comprise a metal or metal alloy and, optionally, be shape set to embody a curved (non-linear) form. An exemplary metal alloy that may be used to fabricate the wires 140, 142, 344, 346 includes, without limitation, nitinol. The wire or wire strands may embody a uniform cross-section along a longitudinal length or may have a cross-section that varies along a longitudinal length. The cross-section of the wire or wire strands may be circular, oblong, semicircular, triangular, rectangular, star shaped, or any other cross-section. By way of further example, the wires 140, 142, 344, 346 may comprise a single strand of nitinol having a uniform circular cross-section and an outside diameter ranging between 0.0001 inches and 0.05 inches, such as 0.003 inches. By way of further example, each of the wires may have an overall length that is more than twice the longitudinal dominant dimension of a guide 130, 132, 334, 336.

In this exemplary embodiment, the basket 304 includes four wires 140, 142, 344, 346 that cooperate to form four loops 150, 152, 354, 356 that are repositionable with respect to the sheath 102 to capture objects within an interior of the loops. In exemplary form, the loops may be arranged in a rectangular configuration. By way of example, the first and second wires 140, 142 are joined to one another at a joint 154 in a fixed relationship. This fixed relationship may be the result of welding, gluing, soldering, twisting, weaving, or any other means so that longitudinal repositioning of the first and second wires 140, 142 are not independent of one another at the joined location 154. Alternatively, the first and second wires 140, 142 may comprise an integral single wire upstream from the joint 154 and split off downstream of the joint 154 to form the two separate wires 140, 142. In any event, the upstream portions of the first and second wires 140, 142 are operatively coupled to an anchor 158 associated with at least one of the sheath 102 or a guide 130, 132. As used with respect to this second exemplary extraction device 300, "upstream" refers to portions of the first and second wires 140, 142 between the joint 154 and the anchor 158, where the anchor retains the first and second wires in a fixed location. And as used with respect to this second exemplary extraction device 300, "downstream" refers to portions of the first and second wires 140, 142 between the joint 154 and where the wires are operatively coupled to the line 108. In any event, downstream portions of the first and second wires 140, 142 may extend through one of the guides 130, 132 and may be operatively coupled to the line 108 so that retraction of the line causes retraction of the downstream portions of the first and second wires 140, 142 into the guides 130, 132, whereas extension (longitudinally repositioning the line toward the distal end of the sheath 102) of the line causes extension of the wires 140, 142 further beyond the guides 130, 132. Conversely, upstream portions of the first and second wires 140, 142 extend through a different guide 334 and are operatively coupled to the anchor 158 so that the length of wires extending from the guide 334 is relatively constant.

As mentioned, the downstream portions of the first and second wires 140, 142 extend into respective ones of the guides 130, 132. In exemplary form, the downstream portions of the first and second wires 140, 142 may be freely repositionable along or within a respective guide 130, 132, or one downstream portion of either the first and second wire 140, 142 may be stationary with respect to a guide 130, 132, while the second downstream portion of the first and second wires 140, 142 is freely repositionable and operatively coupled to the line 108. In this fashion, the first and second wires 140, 142 are operative to form the first and second loops 150, 152.

A third of the wires 344 may also be operatively coupled to the line 108 and may be operative to form the third loop 354. By way of example, opposing ends of the third wire 344 extend through respective ones of the guides 132, 336. In a case where the first and second wires 140, 142 are freely repositionable within a respective guide 130, 132, at least one opposing end of the third wire 344 may be fixedly mounted to the anchor 158, while the other portion of the third wire may be freely repositionable within the guide 336 (see FIG. 15B). As a result, one guide 336 will accommodate two wires that may be freely repositionable within that guide, while two other guides 130, 132 may have one wire 140, 142 freely repositionable therein and a second wire 344, 346 not freely repositionable therein, while a fourth guide 334 will accommodate two wires that may be fixed in position with respect to that guide via the anchor 158. In exemplary form, respective wires 14, 142, 344 may be mounted to the anchor 158 using various forms of attachment or bonding such as, without limitation, adhesives, welding, and brazing.

Finally, a fourth of the wires 346 may also be operatively coupled to the line 108 and is operative to form the fourth loop 356. By way of example, opposing portions of the fourth wire 346 extend through respective ones of the guides 130, 336. In a case where the first and second wires 140, 142 are freely repositionable within a respective guide 130, 336, at least one portion of the fourth wire 344 is fixedly mounted to the anchor 158, while the other end of the fourth wire is freely repositionable within a guide 336. As a result, this guide 336 will accommodate two wires that are freely repositionable within that guide, while an adjacent guide 130 may have one wire 140 freely repositionable therein and a second wire 346 not freely repositionable therein. In exemplary form, the fourth wire 346 may be fixedly mounted to the anchor 158 using adhesive 160 or any other means of bonding such as, without limitation, welding and brazing. As referenced previously, the line 108 is operatively coupled to at least three of the four wires 140, 142, 344, 346 so that operation of the handle control 106 by an operator repositions the basket 304 between a retracted/closed position and an open/expanded position. By way of example, the line 108 may comprise any number of materials and constructions such as, without limitation, metals, metal alloys, single wire, multiple wires, whether in parallel, twisted, or braided. In exemplary form, the line 108 comprises a nitinol single wire having a circular cross-section and having a diameter of approximately 0.015 inches. It should be noted, however, that the diameter of the line 108 may be proportional or sized in relation to the size of the sheath 102 so that larger sheath diameters can accommodate larger line diameters and, vice versa, smaller sheath diameters can accommodate smaller line diameters.

In exemplary form, the second exemplary embodiment of a medical extraction device 300 includes a handle control 106 comprising complementary housing halves 202, 204 mounted to one another that may be fixedly or repositionably mounted to the sheath 102. These housing halves 202, 204 delineate an interior region within which a first actuator 210 may be repositioned. The first actuator 210 may extend through an opening 212 within at least one of the halves 202, 204 (the halves 202, 204 may also cooperate to delineate the opening 212) and may be operatively coupled to the line 108. In this fashion, repositioning of the actuator 210 may cause longitudinal repositioning of the line 108 with respect to the sheath 102. And this longitudinal motion of the line 108 is correspondingly carried over into motion of at least three of the four wires 140, 142, 344, 346 to expand and retract the basket 304. In this exemplary embodiment, travel of the first actuator 210 may be limited so that its range of motion corresponds with the range of expanding and retracting of the basket 304. In other words, when the first actuator 210 is at one end of its range of motion, the basket 304 may be fully retracted, whereas the basket may be fully expanded when the first actuator is at its opposite end of its range of motion. Consequently, repositioning of the first actuator 210 is operative to manipulate the relative shape of the basket 304.

It is also within the scope of the disclosure to operatively couple the line 108 to the housing halves 202, 204, rather than to the first actuator 210, where the housing halves are repositionable with respect to the sheath 102 and may be spring biased with respect thereto so as to provide either a biased open or biased closed basket 304 position. In such a circumstance, the first actuator 210 may be operatively coupled to the sheath 102. Accordingly, longitudinal motion of the housing halves 202, 204 with respect to the sheath 102 may be operative to transmit corresponding longitudinal motion to the line(s) 108 with respect to the sheath 102. And this longitudinal motion of the line(s) 108 is correspondingly carried over into motion of at least three of the four wires 140, 142, 344, 346 (and optionally all four wires) to open and close the basket 304.

In either exemplary control discussed immediately above, travel of the first actuator 210 or housing halves 202, 204 relative to the sheath 102 may be limited so that this range of motion/travel corresponds with the range of travel between fully extending and fully retracting (i.e., opening and closing) the basket 304. In other words, when the first actuator 210 or housing halves 202, 204 is at one end of its range of motion relative to the sheath 102, the basket 304 may be fully retracted, whereas the basket may be fully extended when the first actuator or housing halves is at its opposite end of its range of motion relative to the sheath. Consequently, repositioning of the first actuator 210 or the housing halves 202, 204 relative to the sheath 102 is operative to manipulate the relative shape of the basket 304 by repositioning the basket between a fully retracted position and a fully expanded position.

Though not required, the handle control 106 may include a second actuator 220 that is also repositionable with respect to the housing halves 202, 204. In a circumstance where one or more of the guides 130, 132, 334, 336 are not rigidly mounted to the sheath 102, and can be longitudinally repositionable with respect to the sheath, the second actuator 220 may be operatively coupled to a hollow conduit 230 that extends along an interior of the sheath 102. In exemplary form, the conduit 230 may have an external maximum dimension that is smaller than the smallest internal dimension of the sheath 102, thereby allowing the conduit to be longitudinally repositionable with respect to the sheath. Moreover, the conduit 230 may have a continuous internal cavity that extends longitudinally through which the line 108 may extend. In such a circumstance, the line 108 may be independently longitudinally repositionable with respect to the conduit 230 and the sheath 102. Similarly, the conduit 230 may be independently longitudinally repositionable with respect to the line 108 and the sheath 102. In this fashion, longitudinal motion of the second actuator 220 is operative to transmit corresponding longitudinal motion to the conduit 230 within the sheath 102. And this longitudinal motion of conduit 230 is correspondingly carried over into motion of the guides 130, 132, 334, 336 to extend and retract the guides with respect to the sheath 102. In this exemplary embodiment, travel of the second actuator 220 may be limited so that its range of motion corresponds with the range of extending and retracting of the guides 130, 132, 334, 336 with respect to the sheath 102. In other words, when the second actuator 220 is at one end of its range of motion, the guides 130, 132, 334, 336 may be fully (or nearly fully) retracted within the sheath 102, whereas the guides 130, 132, 334, 336 may be fully extended (out or nearly out) of the sheath 102 when the second actuator is at its opposite end of its range of motion. Consequently, repositioning of the second actuator 220 distally is operative to manipulate the relative shape of the basket 304.

The foregoing second medical extraction device 300 may be utilized to extract various objects from within an interior of an anatomical cavity. By way of exemplary explanation, use of the extraction device 300 will be explained in the context of a renal kidney stone removal procedure. Nevertheless, those skilled in the art will understand that use of the medical extraction device 300 shall not be limited to renal kidney stone removal procedures, but rather that this description is just one of numerous procedures for which the extraction device 300 has application.

Figure 16:
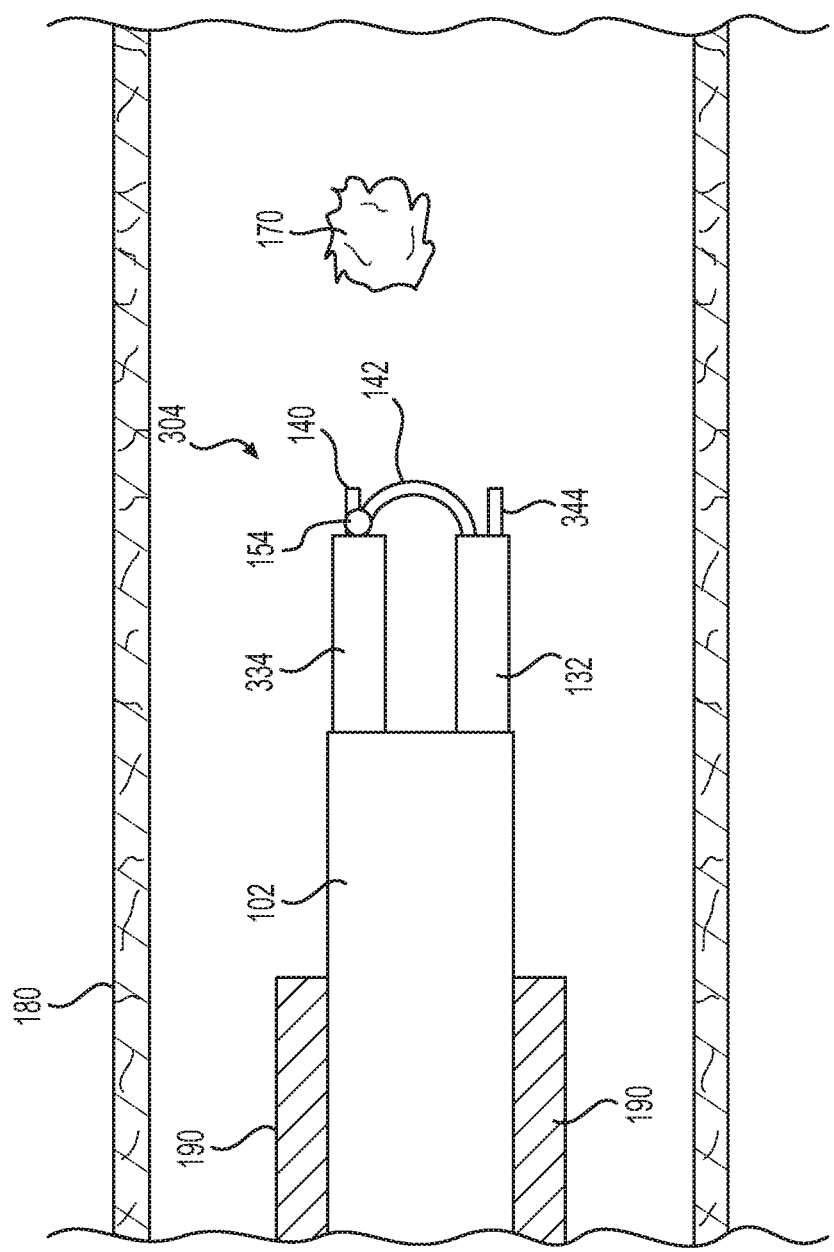
FIG. 16 is a profile view of a distal end of the second exemplary medical extraction device extending through a ureteroscope within a renal path just with the basket in a retracted position.

Initially, a suitable renal path 180 to the kidney in the patient's body may be explored and appropriate visualization may also be provided by means of a scope 190 (e.g., ureteroscope) traversing the renal path. Upon approximating the location of a target object 170 (e.g., a kidney stone), the basket 304 end of the extraction device 300, coupled to the sheath 102, may be advanced through the scope 190 while the basket is in a retracted position, as shown in FIG. 16, to advance the basket and distal end of the sheath beyond a distal end of the scope 190. Continued advancing of the sheath 102 and basket 304 may continue until the basket 304 reaches the targeted area where the object 170 to be removed is located. After the basket 304 reaches the desired area as determined by visual inspection of the scope 190, an operator may grasp the handle control 106 (i.e., complementary housing halves 202, 204) and repositions one or both of the actuators 210, 220 relative to the housing halves 202, 204 (or reposition the handle housings with respect to the sheath) to reposition the line 108 relative to the sheath 102, thereby repositioning the basket from its retracted position toward an open position.

Figure 17:
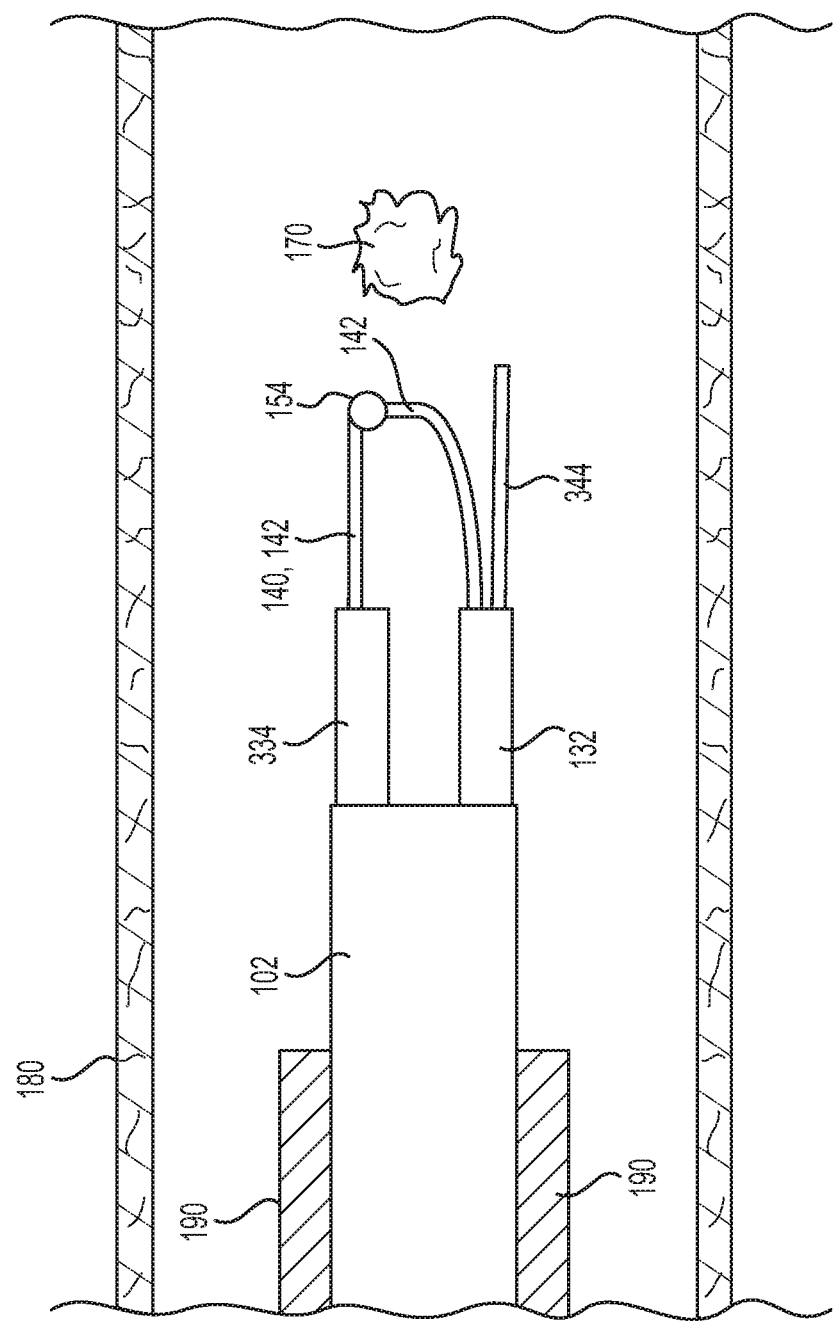
FIG. 17 is a profile view of the distal end of the second exemplary medical extraction device extending through a ureteroscope within a renal path with the basket open to receive the object to be removed.
Figure 18:
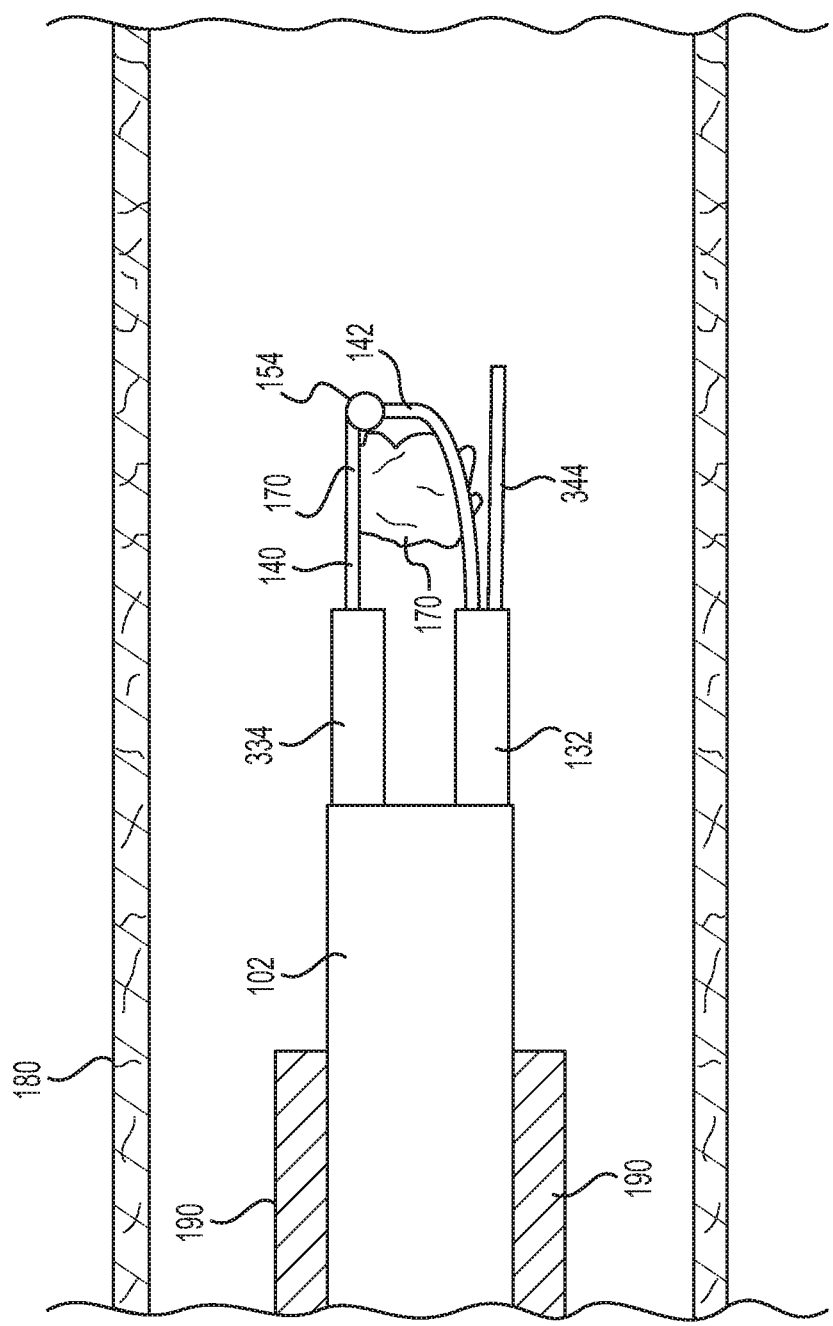
FIG. 18 is a profile view of the distal end of the second exemplary medical extraction device extending through a ureteroscope within a renal path with the basket open and receiving the object to be removed.
Figure 19:
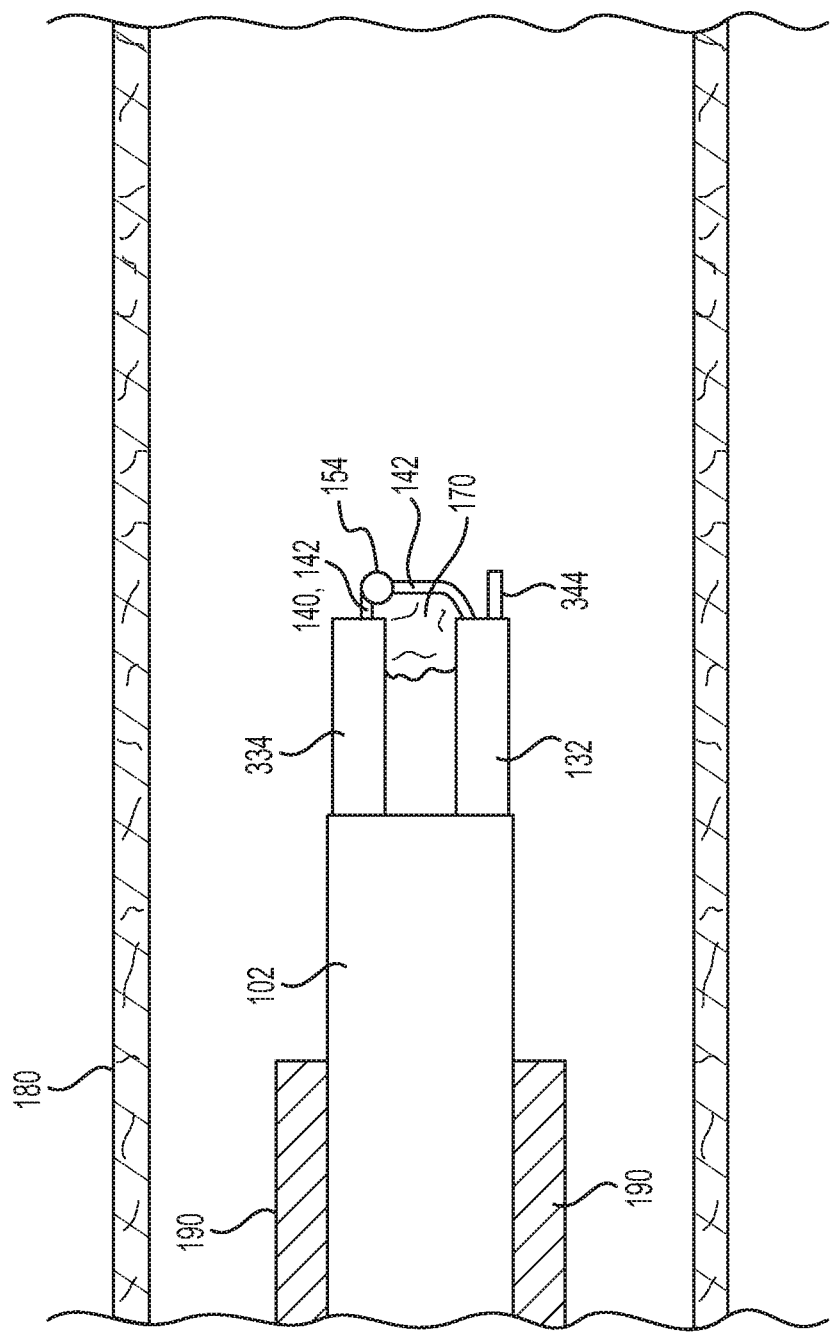
FIG. 19 is a profile view of the distal end of the second exemplary medical extraction device extending through a ureteroscope within a renal path with the basket retracted to retain the object to be removed.
Figure 25:
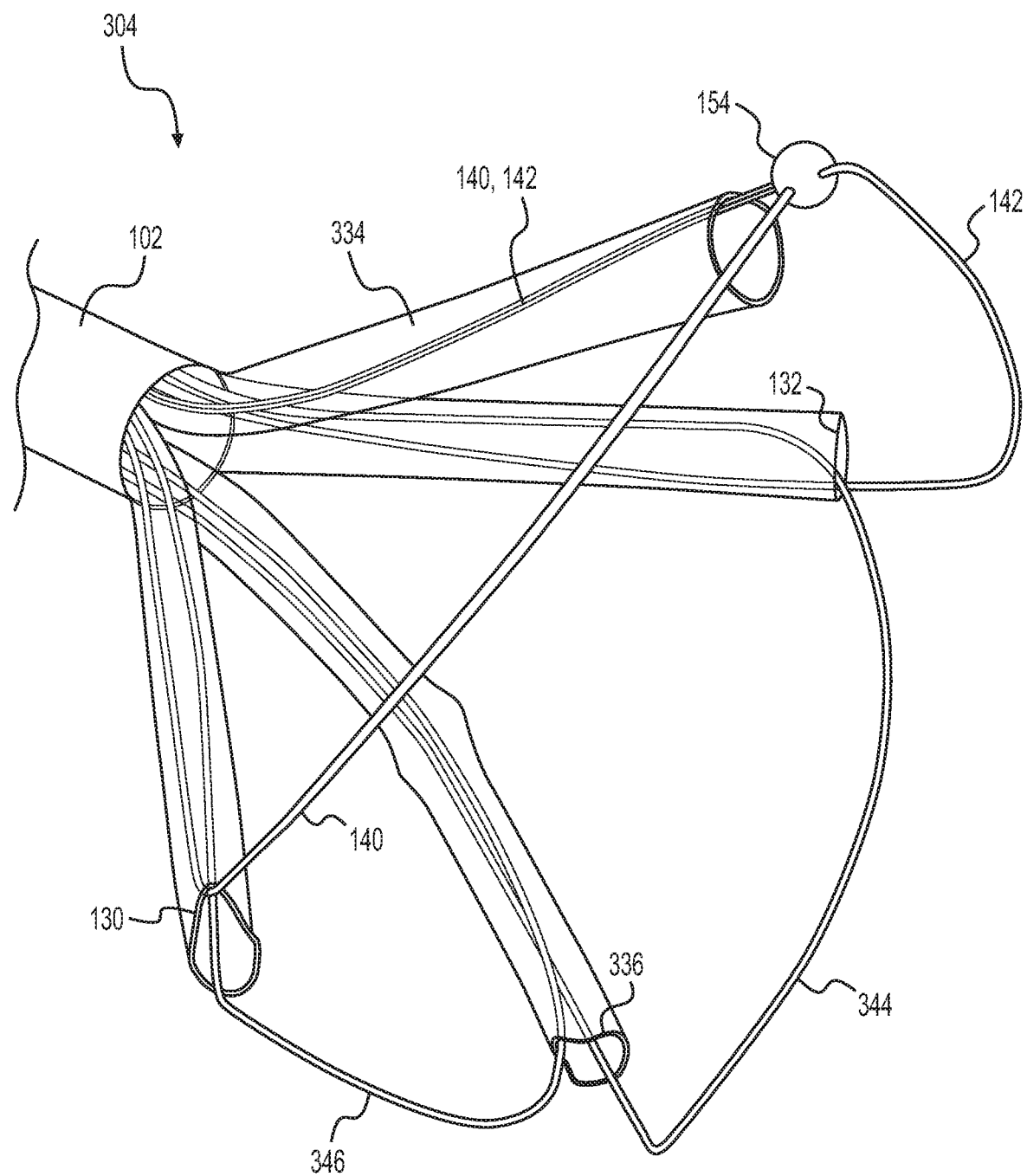
FIG. 25 is an elevated perspective view of the basket of the second exemplary medical extraction device of FIG. 11 in an open or expanded position.
Figure 26:
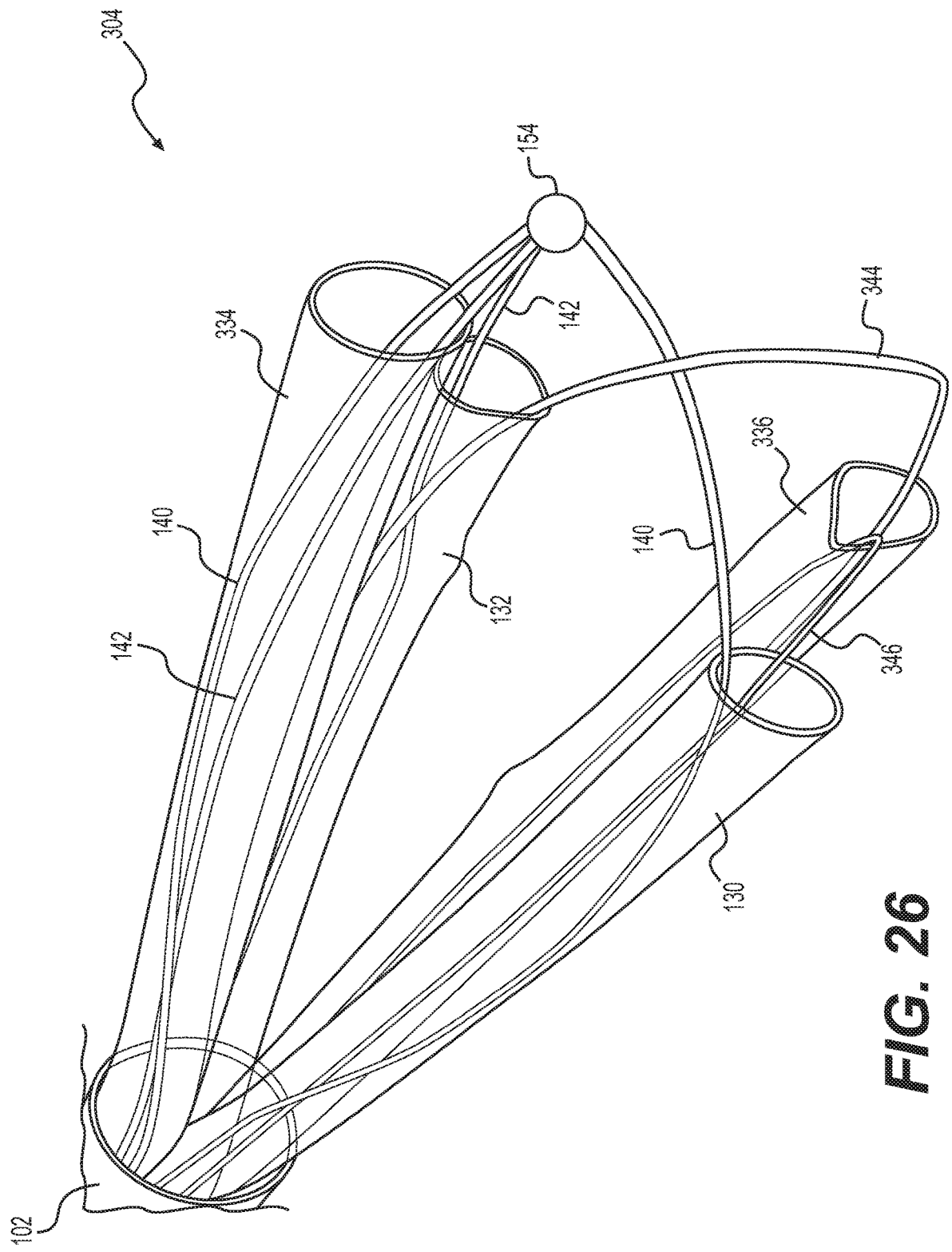
FIG. 26 is an elevated perspective view of the basket of the second exemplary medical extraction device in an intermediate position between the closed and open positions.
Figure 27:
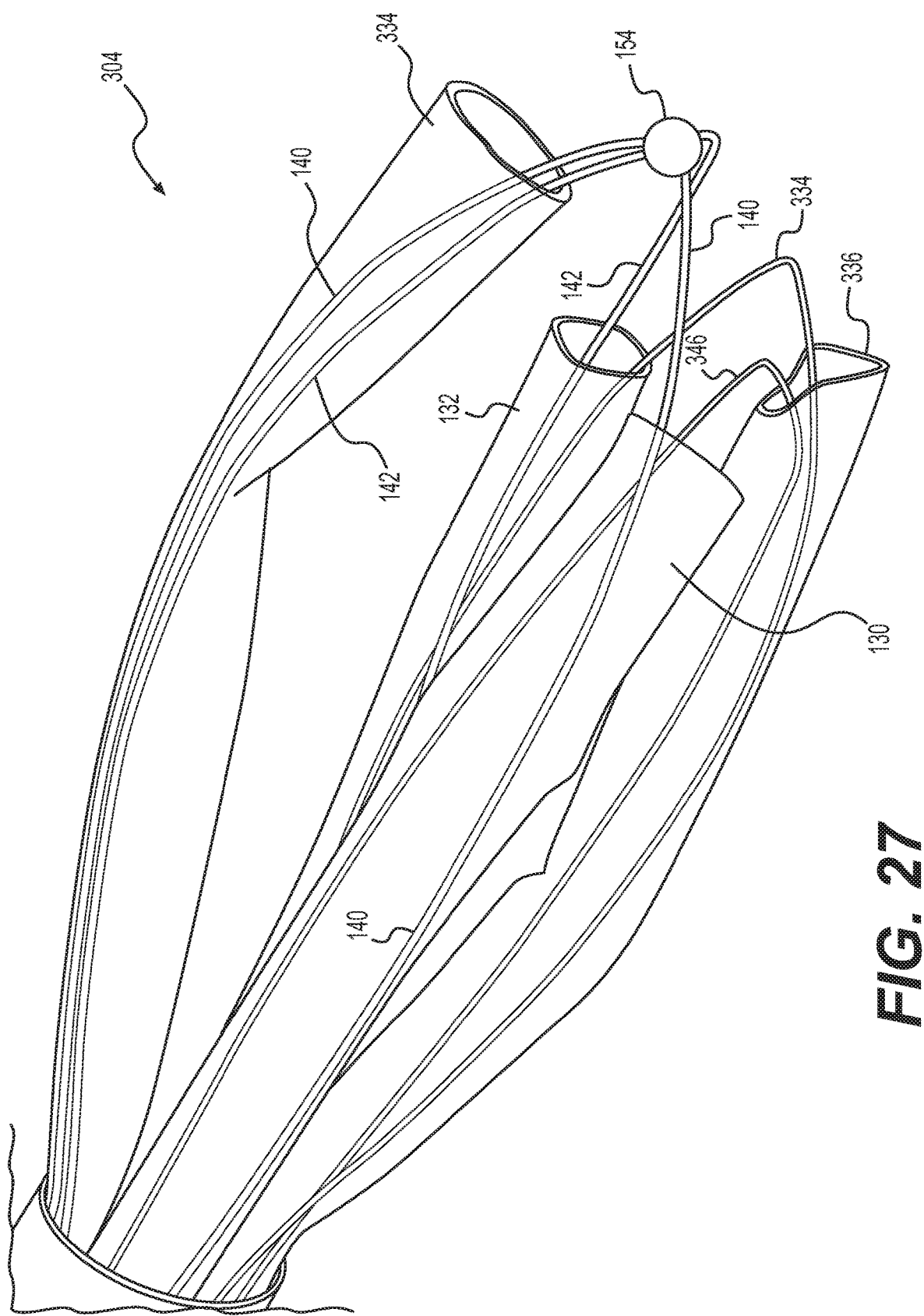
FIG. 27 is an elevated perspective view of the basket of the second exemplary medical extraction device in a closed or retracted position.
Figure 28:
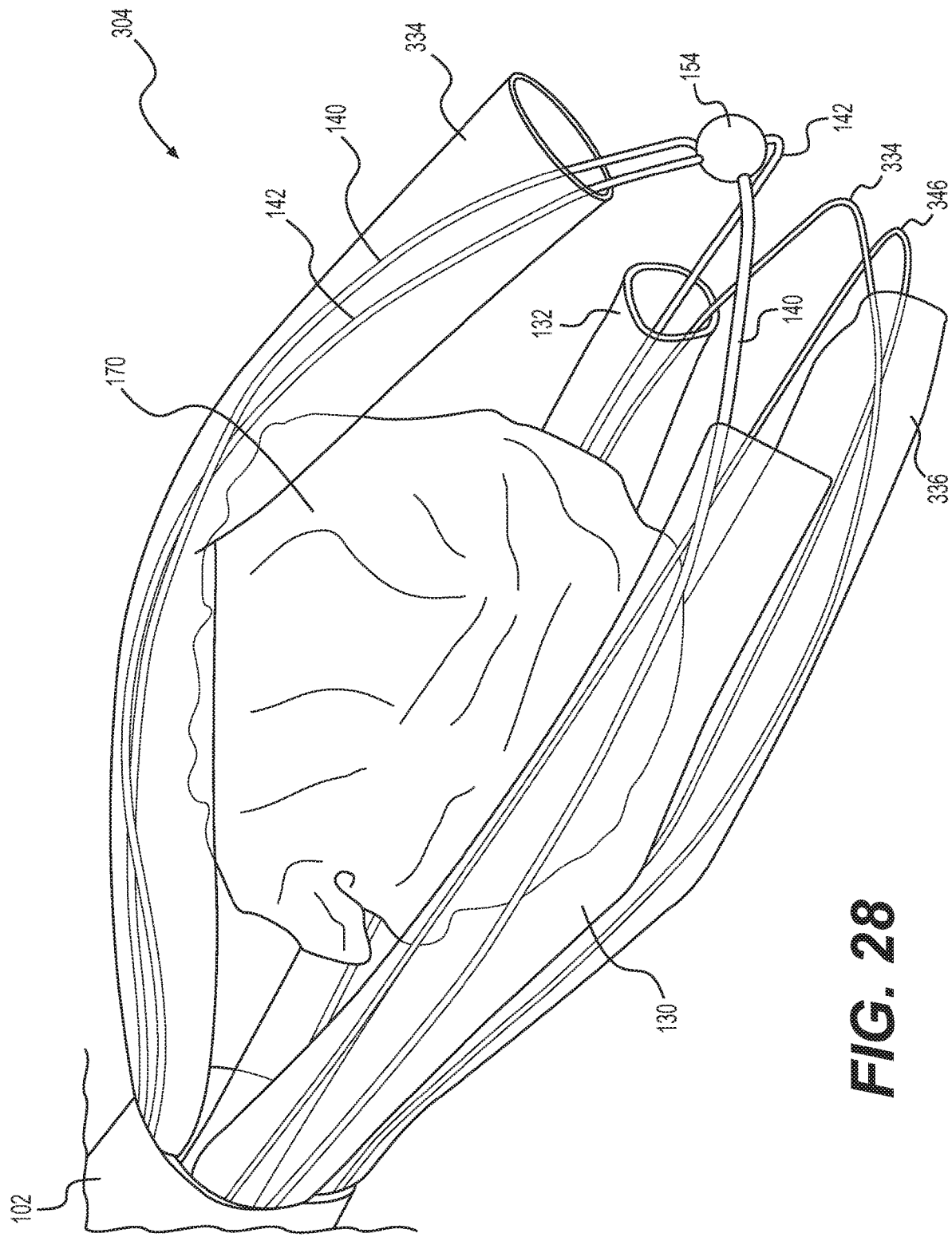
FIG. 28 is an elevated perspective view of the basket of the second exemplary medical extraction device in a closed or retracted position, but with an object captured by the basket.

In a circumstance where the handle control 106 includes a second actuator 220, the second actuator and the first actuator 210 may be concurrently repositioned or repositioned independent of one another to move the basket from a closed or retracted position to an open or expanded position. In exemplary form, the second actuator 220 may be repositioned distally (toward the basket 304 and with respect to the handle housings 202, 204), thereby causing the conduit 230 to move longitudinally through the sheath 102 and direct the guides 130, 132, 334, 336 to extend beyond (or further beyond) the sheath. The operator of the handle control 106 may then reposition the first actuator 210 distally (toward the basket 304 and with respect to the handle housings 202, 204), thereby causing the line 108 to move longitudinally through the sheath 102 and cause the wire 140, 142, 344, 346 lengths extending beyond the guides 130, 132, 334, 336 to increase as well size of the loops. FIGS. 17 and 25 depict an exemplary position of the basket 304 where the guides 130, 132, 334, 336 are at least partially extended from the sheath 102 (via the second actuator 220, or by default if not actuated) and the wires 140, 142, 344, 346 are at least partially extended, which coincides with a partially open or fully open (i.e., expanded) position. This open or expanded position may be maintained while the entire distal portion of the extraction device 300 is repositioned so that the target object 170 intending to be captured (e.g., a kidney stone) may be received within the open basket 304, as shown in FIG. 18.

FIG. 16 depicts an exemplary position of the basket 304 where the guides 130, 132, 334, 336 are partially extended from the sheath 102 (via the second actuator 220) and the wires 140, 142, 344, 346 are partially extended, which wire position coincides with the retracted position. This retracted position may be maintained while the entire distal portion of the extraction device 300 is repositioned to get in proximity to the target object 170 (e.g., a kidney stone). When the basket 304 is in proximity to the target object 170, as depicted in FIG. 17, the first actuator 210 may be repositioned relative to the housing halves 202, 204 to expand or open the basket 304. Post opening of the basket 304, the basket may be further positioned distally so that the targeted object 170 is received within the open basket, as depicted in FIG. 18.

After the object 170 is at least partially received within the open basket 304, the first actuator 210 may be repositioned proximally (away from the basket 304 and with respect to the handle housings 202, 204), thereby causing the line 108 to move longitudinally through the sheath 102 and causing the wire lengths 140, 142, 344, 346 extending beyond the guides 130, 132, 334, 336 to decrease, as well as decreasing the wire length associated with the loops 150, 152, 354, 356. This decreased length of the wires 140, 142, 344, 346 coincides with the joint 154 forming a tip that arches over and moves in an arcuate path to come behind the targeted object 170, which creates a backstop to preclude the object from backing out of the basket 304 (see FIGS. 19, 28, and 30). Depending upon the size of the object 170 and the operator's confidence as to whether the object will stay within the basket 304 upon relocating the entire distal portion of the extraction device 300 proximally (for eventual removal of the basket 304 and target object 170 from the renal path 180), the operator may reposition the second actuator 220 distally (toward the basket 304), thereby causing the guides 130, 132, 334, 336 to move further longitudinally through the sheath 102 and cause the wire lengths 140, 142, 344, 346 extending beyond the guides 130, 132, 334, 336 to decrease as well as decreasing the wire length associated with the loops 150, 152, 354, 356 to tighten the loops 150, 152, 354, 356 around the object (see FIG. 28). Post capturing the target object 170 within the basket 304, the extraction device 300 and target object may be removed from the renal path 180.

Alternatively, in a circumstance where the guides 130, 132, 334, 336 are not repositionable with respect to the sheath 102, the first actuator 210 may be repositioned to move the basket from a closed or retracted position to an open or extended position upon reaching the target object 170. In exemplary form, the operator of the handle control 106 may reposition the first actuator 210 distally (toward the basket 304), thereby causing the line 108 to move longitudinally through the sheath 102 and cause the wire 140, 142, 344, 346 lengths extending beyond the guides 130, 132, 334, 336, thereby increasing the length of each loop 150, 152, 354, 356 extending from the sheath. FIGS. 17 and 25 depict an exemplary position of the basket 304 where the guides 130, 132, 334, 336 are partially extended from the sheath 102 and the wires 140, 142, 344, 346 are extended from the guides and sheath, which coincides with an open or expanded position of the basket. This open or expanded position may be maintained while the entire distal portion of the extraction device 300 is repositioned further distally so that the targeted object 170 to be captured (e.g., a kidney stone) may be received within the open basket 304, as shown in FIG. 18. After the target object 170 is at least partially received within the open basket 304, the first actuator 210 may be repositioned proximally (away from the basket 304), thereby causing the line 108 to move longitudinally through the sheath 102 and causing the wire lengths 140, 142, 344, 346 extending beyond the guides 130, 132, 334, 336 to decrease as well as decrease the wire lengths associated with the loops 150, 152, 354, 356. This decreased length of the wires 140, 142, 344, 346 coincides with the joint 154 forming a tip that arches over and moves in an arcuate path to come behind the target object 170, which creates a backstop to preclude the target object from backing out of the basket 304 (see FIGS. 19, 28, and 30). After the joint 154 has been repositioned behind the target object 170, the extraction device 300 and object 170 may be removed from the renal path 180.

It is also within the scope of the disclosure to reposition the actuator 210 in an opposite direction compared to those described previously in a circumstance where the actuator 210 is mounted to the sheath 102 and the line 108 is mounted to the housing halves 202, 204. By way of example, in such a circumstance, the first actuator 210 may be repositioned proximally (away from the basket 104 and with respect to the handle housings 202, 204) to open or expand the basket and distally (toward the basket) to retract or close the basket.

Figure 20:
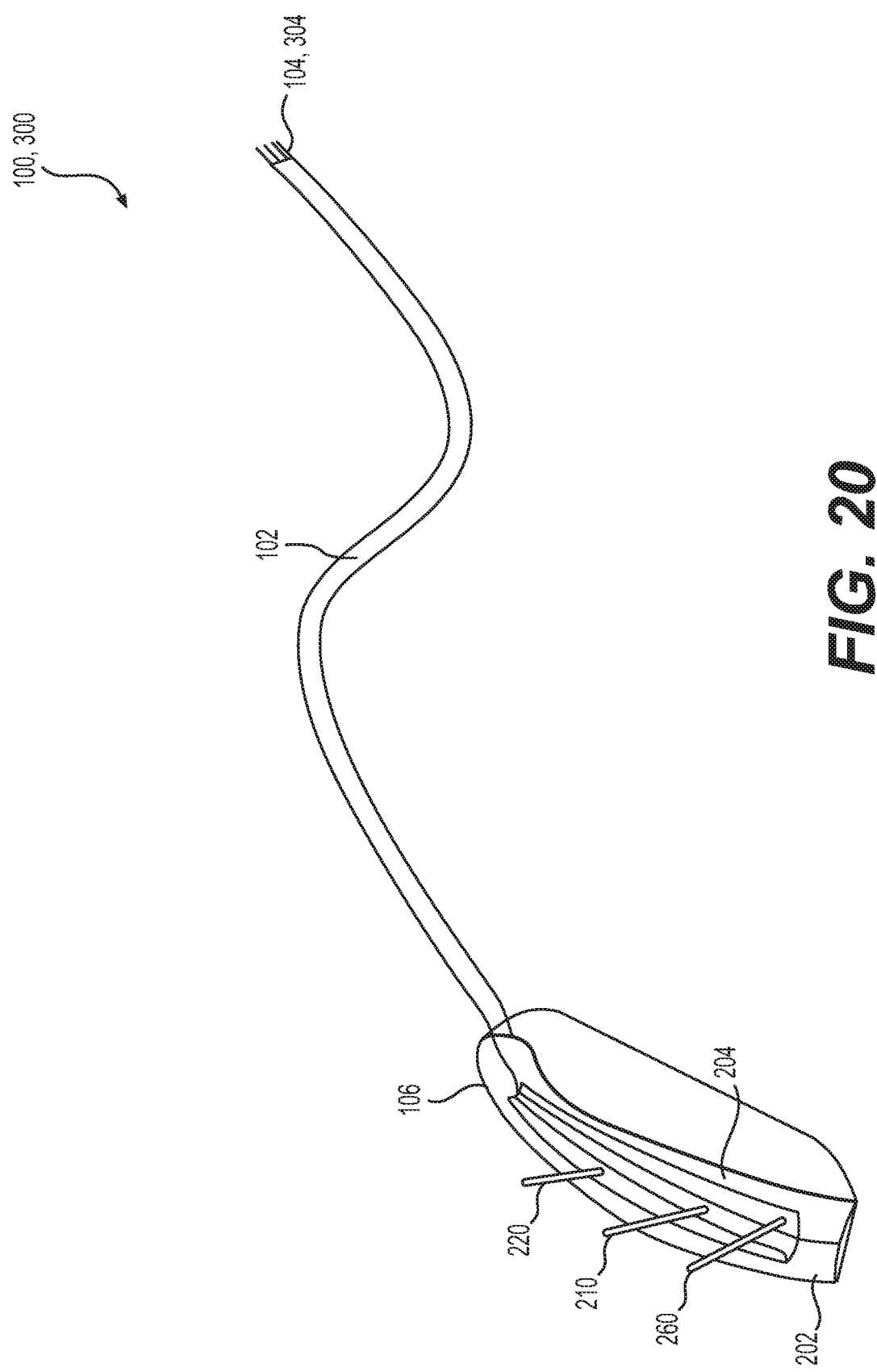
FIG. 20 is an elevated perspective view of an alternate exemplary embodiment of the first and second exemplary medical extraction devices in accordance with the instant disclosure.
Figure 21:
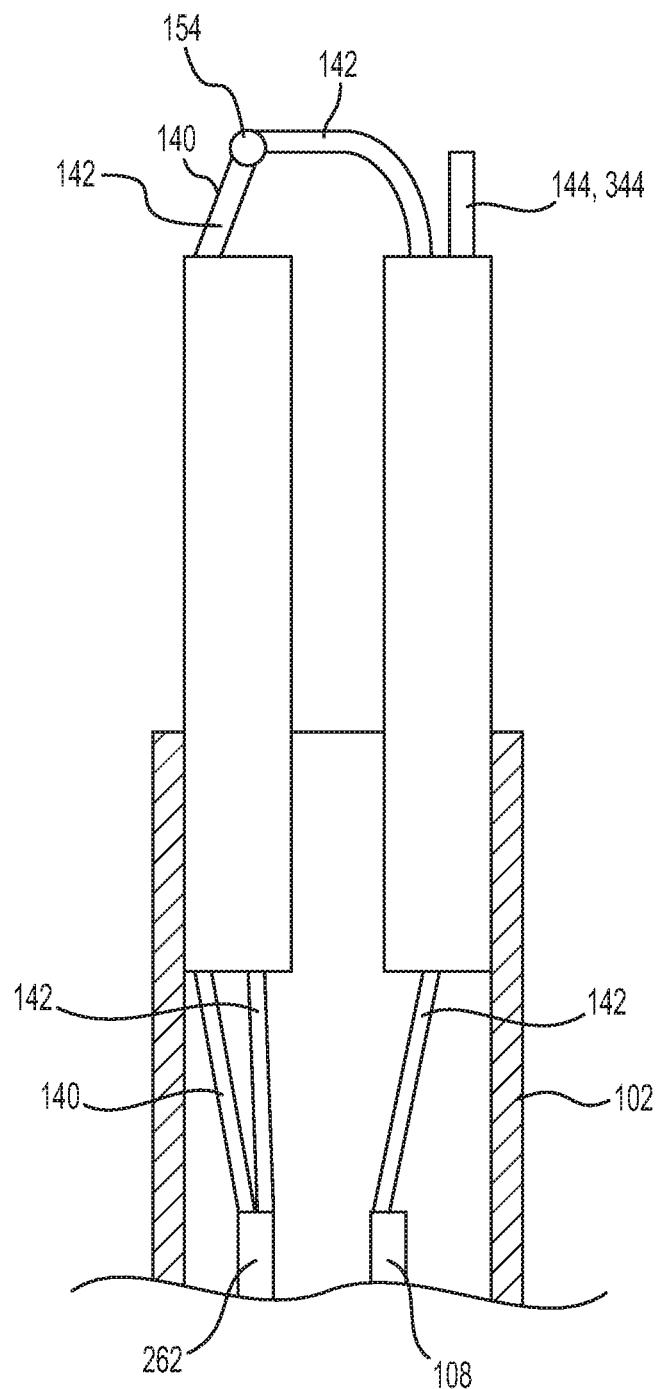
FIG. 21 is a cross-sectional view of the exemplary sheath and a perspective view of certain other exemplary components extending through the sheath where the device includes dual lines and separate actuators for each line.

As depicted in FIGS. 20 and 21, it is also within the scope of the disclosure to provide a third control 260 as part of the handle control 106 of the extraction device 100, 300. This third control 260 may be mounted to a second line 262 that extends through the sheath 102 and is operatively coupled to portions of at least one of the wires 140, 142, 144, 344, 346 that might otherwise be coupled to the anchor 158. In this manner, to the extent an operator of the device 100, 300 desires to have the joint 154 extend further outward during the retention of the target object 170, the operator may reposition the third control 260 distally (toward the basket 104, 304) or proximally (away from the basket) in order to cause the joint 154 to be repositioned further from or closer to one or more of the guides 130, 132, 334, 336.

It should also be understood that while each basket 104, 304 has been exemplary described with a single joint, it is also within the scope of the disclosure for the baskets 104, 304 to have multiple joints where respective loops are coupled to one another. Each additional joint may be created similarly to the joints 154 disclosed herein.

It should further be understood that while each extraction device 100, 300 has been described as having an anchor 158, it is within the scope of the disclosure to provide these extraction devices 100, 300 with multiple anchors where each anchor is mounted to one or more wires.

Following from the above description and invention summaries, it should be apparent to those of ordinary skill in the art that, while the methods and apparatuses herein described constitute exemplary embodiments of the present invention, it is to be understood that the inventions contained herein are not limited to the above precise embodiment and that changes may be made without departing from the scope of the invention as defined by the following proposed points of novelty. Likewise, it is to be understood that it is not necessary to meet any or all of the identified advantages or objects of the invention disclosed herein in order to fall within the scope of the invention, since inherent and/or unforeseen advantages of the present invention may exist even though they may not have been explicitly discussed herein.

What is claimed is:

1. A medical extraction device comprising:
 a hollow sheath including a distal end from which a basket may extend in an expanded position, the basket repositionable between a retracted position and the expanded position, the basket comprising:
  a first guide and a second guide circumscribed by the hollow sheath;
  a first loop, a second loop, and a third loop, where the first loop extends between the first and second guides;
  a first anchor point fixing a relative position of an upstream portion of the second loop with respect to an upstream portion of the third loop;
  a first joint coupling the second loop and the third loop downstream from the first anchor point;
  a second anchor point fixing a relative position of an upstream portion of the first loop with respect to a portion of the first guide;
  a line operatively coupled to downstream portions of at least two of the first, second, and third loops so that repositioning of the line is operative to at least one of increase and decrease the length of the at least two of the first, second, and third loops extending from the distal end of the hollow sheath.

2. The medical extraction device of claim 1, further comprising a fourth loop and a third guide, wherein:
the second loop extends between the second and third guides.

3. The medical extraction device of claim 1, further comprising a handle control mounted to a proximal portion of the hollow sheath and configured to be handheld, the handle control including an actuator operatively coupled to the line so that repositioning of the actuator is operative to direct repositioning of the line.

4. The medical extraction device of claim 1, further comprising a handle control repositionably mounted to a proximal portion of the hollow sheath, the handle control operatively coupled to the line so that repositioning of the handle control with respect to the hollow sheath is operative to direct repositioning of the line.

5. The medical extraction device of claim 1, wherein the line comprises a plurality of lines, each of the plurality of lines being operatively coupled to at least one of the first, second, and third loops.

6. The medical extraction device of claim 1, wherein at least one of the first and second guides comprises a duct through which extends portions of the at least two of the first, second, and third loops.

7. The medical extraction device of claim 1, wherein:
the first guide comprises a first duct through which portions of the first loop and the second loop extend; and,
the second guide comprises a second duct through which portions of the first loop and the second loop extend.

8. The medical extraction device of claim 1, wherein at least one of the first and second guides delineates a channel along which extends portions of the at least two of the first, second, and third loops.

9. The medical extraction device of claim 1, wherein:
the first guide comprises a first channel along which portions of the first loop and the second loop extend; and,
the second guide comprises a second channel along which portions of the first loop and the second loop extend.

10. The medical extraction device of claim 1, wherein at least one of the first, second, and third loops is discontinuous.

11. The medical extraction device of claim 1, wherein the first guide and the second guide are at least one of repositionable and fixedly positioned with respect to the hollow sheath.

12. The medical extraction device of claim 1, wherein the first joint includes at least one of a weld, glue, solder, a wire twist, and a wire weave.

13. The medical extraction device of claim 1, wherein a downstream portion of the first loop and a downstream portion of the third loop are freely repositionable with respect to the second guide.

14. The medical extraction device of claim 1, wherein the first loop is independently repositionable with respect to the second and third loops.

15. The medical extraction device of claim 1, wherein the first loop is dependently repositionable with respect to the second and third loops by way of the line.

16. The medical extraction device of claim 1, wherein the first anchor point comprises at least one of a weld, glue, solder, a wire twist, and a wire weave secured to at least one of the first guide, the second guide, and the hollow sheath.

17. The medical extraction device of claim 1, wherein the first anchor point and the second anchor point comprise a common anchor.

18. A medical extraction device comprising:
a sheath including a distal end configured to be inserted into a patient and a proximal end configured to be retained exteriorly of the patient;
a basket configured to extend from the distal end of the sheath and be repositionable between an expanded position and a retracted position, the basket including at least three loops, the basket also including a first guide and a second guide, where the first guide receives portions of the first loop and the third loop, where the second guide receives portions of the first loop and the second loop, where the second loop and the third loop are fixedly mounted to one another at a location interposing the first guide and the second guide; and,
a handle control operatively coupled to a proximal end of the sheath and being operatively coupled to the basket, the handle control configured to facilitate repositioning of the basket with respect to the sheath between the retracted position and the expanded position.

19. The medical extraction device of claim 18, further comprising a third guide and where the at least three loops comprises a fourth loop.

20. The medical extraction device of claim 18, wherein the handle control includes an actuator operatively coupling a line to proximal portions of at least two of the first, second, and third loops so that repositioning of the line is operative to at least one of increase and decrease the length of the at least two of the first, second, and third loops extending from the distal end of the sheath.

21. The medical extraction device of claim 20, wherein the line comprises a plurality of lines, each of the plurality of lines being operatively coupled to at least one of the first, second, and third loops.

22. The medical extraction device of claim 18, wherein at least one of the first and second guides comprises a duct through which extends portions of at least two of the first, second, and third loops.

23. The medical extraction device of claim 18, wherein:
the first guide comprises a first duct through which portions of the first loop and the third loop extend; and,
the second guide comprises a second duct through which portions of the first loop and the second loop extend.

24. The medical extraction device of claim 18, wherein at least one of the first and second guides delineates a channel along which extends portions of at least two of the first, second, and third loops.

25. The medical extraction device of claim 18, wherein at least one of the first, second, and third loops is discontinuous.

26. The medical extraction device of claim 18, wherein the first guide and the second guide are at least one of repositionable and fixedly positioned with respect to the sheath.

27. The medical extraction device of claim 18, wherein the second loop and the third loop are mounted to one another at a first joint, where the first joint includes at least one of a weld, glue, solder, a wire twist, and a wire weave.

28. The medical extraction device of claim 18, wherein a proximal portion of the first loop and a proximal portion of the third loop are freely repositionable with respect to the first guide.

29. The medical extraction device of claim 18, wherein the first loop is independently repositionable with respect to the second and third loops.

30. The medical extraction device of claim 18, wherein the first loop is dependently repositionable with respect to the second and third loops by way of a line.

* * * * *